(12) United States Patent
Ramnauth et al.

(10) Patent No.: US 7,141,595 B2
(45) Date of Patent: Nov. 28, 2006

(54) AMINO BENZOTHIAZOLE COMPOUNDS WITH NOS INHIBITORY ACTIVITY

(75) Inventors: Jailall Ramnauth, Toronto (CA); Suman Rakhit, Mississauga (CA); Shawn Maddaford, Mississauga (CA); Namrta Bhardwaj, Etobicoke (CA)

(73) Assignee: Neuraxon Inc., Toronto (CA)

( * ) Notice: Subject to any disclaimer, the term of this patent is extended or adjusted under 35 U.S.C. 154(b) by 2 days.

(21) Appl. No.: 10/995,146

(22) Filed: Nov. 24, 2004

(65) Prior Publication Data

US 2005/0209291 A1   Sep. 22, 2005

Related U.S. Application Data

(63) Continuation-in-part of application No. PCT/CA03/01185, filed on Aug. 7, 2003.

(60) Provisional application No. 60/401,333, filed on Aug. 7, 2002.

(51) Int. Cl.
*A61K 31/428* (2006.01)
*A61K 31/4402* (2006.01)
*A61K 31/5377* (2006.01)
*C07D 277/82* (2006.01)
*C07D 213/24* (2006.01)
*C07D 295/03* (2006.01)

(52) U.S. Cl. .................. 514/367; 514/321; 514/235.2; 548/161; 548/164; 546/198; 544/135

(58) Field of Classification Search ................ 548/146, 548/164, 161; 514/323, 367, 321, 235.2; 546/198, 209; 544/135
See application file for complete search history.

(56) References Cited

U.S. PATENT DOCUMENTS 5,677,321 A   10/1997   Jeon et al.
6,156,777 A   12/2000   Rohde et al.
2003/0134859 A1 * 7/2003 Amemiya et al. .......... 514/247

FOREIGN PATENT DOCUMENTS

| EP | 0282971 | 9/1988 |
|----|---------|--------|
| WO | WO 95/09619 | 4/1995 |
| WO | WO 97/15306 | 5/1997 |
| WO | WO 00/69838 | 11/2000 |
| WO | WO 01/94325 | 12/2001 |

OTHER PUBLICATIONS

Landquist, J., "Diaminobenzobisthiazoles and related compounds", Journal of the Chemical Society Section C, 1967, pp. 2212-2220, vol. 21.
Hammer, N.A., et al., "Effect of riluzole on acute pain and hyperalgesia in humans", British Journal of Anaesthesia, 1999, pp. 718-722, vol. 82, No. 5.
Kretschmer, B.D., et al., "Riluzole, a glutamate release inhibitor, and motor behavior", Naunyn-Schmiedeberg's Arch Pharmacol, 1998, pp. 181-190, vol. 358.
Keita, H., et al., "Anesthetic concentrations of riluzole inhibit neuronal nitric oxide synthase activity, but not expression, in the rat hippocampus", Brain Research, 2000, pp. 237-240, vol. 881.
Marrannes, R. et al., "Influence of Lubeluzole on Voltage-Sensitive $Ca^{++}$ Channels in Isolated Rat Neurons", The Journal of Pharmacology and Experimental Therapeutics, 1998, pp. 201-214, vol. 286, No. 1.
Andrews, J., et al., "Ascend Pharmaceuticals: Product Focused Innovations in CNS", May 2004.
STN Registry™ and Chemical Abstracts™ Search Transcript, Aug. 6, 2003, pp. 37, 45, 49, 55, 82, 92, 95, 110, 113, 126.
STN Registry™ and Chemical Abstracts™ Search Transcript, Sep. 6, 2001.
STN Registry™ and Chemical Abstracts™ Search Transcript, Jul. 25, 2002.

* cited by examiner

*Primary Examiner*—Kamal A. Saeed
*Assistant Examiner*—Michael P. Barker
(74) *Attorney, Agent, or Firm*—Patricia Folkins

(57) ABSTRACT

The present invention provides novel amino benzothiazole compounds, compositions comprising these compounds and methods of using these compounds as neuroprotectants. In particular, the compounds described in the present invention are useful for treating stroke and neuropathic pain.

85 Claims, 7 Drawing Sheets

AMINO BENZOTHIAZOLE COMPOUNDS WITH NOS INHIBITORY ACTIVITY

FIELD OF THE INVENTION

The present invention relates to novel amino benzothiazole compounds having nitric oxide synthase (NOS) inhibitory activity, to pharmaceutical and diagnostic compositions containing them and to their medical use, particularly as neuroprotectants and for the treatment of neuropathic pain.

BACKGROUND OF THE INVENTION

Nitric oxide (NO) has diverse roles both in normal and pathological processes including the regulation of blood pressure, in neurotransmission, and in the macrophage defense systems (Snyder, S. H., et al., *Scientific American*, May 1992, 68). NO is synthesized by three isoforms of nitric oxide synthase (NOS), two of which, one in endothelial cells (eNOS) and one in neuronal cells (nNOS), are constitutive, and the one, in macrophage cells, which is inducible (iNOS). These enzymes are homodimeric proteins that catalyzed a five-electron oxidation of L-arginine, yielding NO and citrulline. The role of NO produced by each of the NOS isoforms is quite unique. Overstimulation or overproduction of individual NOS isoforms plays a role in several disorders including septic shock, arthritis, diabetes, ischemia-reperfusion injury, pain and various neurodegenerative diseases (Kerwin, J. F. Jr., et al., *J. Med. Chem.* 1995, 38, 4343). For example, the role of NO in cerebral ischemia can be protective or destructive depending on the stage of evolution of the ischemic process and on the cellular compartment producing NO (Dalkara, T., et al. *Brain Pathology*, 1994, 4, 49). While the NO produced by eNOS is likely beneficial by acting as a vasodilator to improve blood flow to the affected area (Huang, Z., et al. *J. Cereb. Blood Flow Metab.* 1996, 16, 981), NO produced by nNOS may contribute to the initial metabolic deterioration of the ischemic penumbra, resulting in larger infarcts (Hara, H., et al., *J. Cereb. Blood Flow Metab.* 1996, 16, 605). The metabolic derangement that occurs during ischemia and subsequent reperfusion results in the expression and release of several cytokines that activate iNOS in several cell types including some of the central nervous system. NO can be produced at cytotoxic levels by iNOS, and increased levels of iNOS contribute to progressive tissue damage in the penumbra, leading to larger infarcts (Parmentier, S., et al. *Br. J. Pharmacol.*, 1999, 127, 546). Inhibition of i-NOS has been shown to ameliorate cerebral ischemic damage in rats (*Am. J. Physiol.*, 268, R286 1995).

NO produced by i-NOS is also thought to play a role in diseases that involve systemic hypotension such as toxic shock and therapy with certain cytokines. It has been shown that cancer patients treated with cytokines such as interleukin 1 (IL-1), interleukin 2 (IL-2) or tumor necrosis factor (TNF) suffer cytokine-induced shock and hypotension due to NO produced from macrophages, i.e., inducible NOS (i-NOS) (*Chemical & Engineering News*, Dec. 20, 33, 1993). i-NOS inhibitors can reverse this. Suppression of adjuvant induced arthritis by selective inhibition of i-NOS is reported in *Eur. J. Pharmacol.*, 273, p. 15–24 (1995).

n-NOS inhibition has also been shown to be effective in antinociception, as evidenced by activity in the late phase of the formalin-induced hindpaw licking and acetic acid-induced abdominal constriction assays (*Br. J. Pharmacol.*, 110, 219–224, 1993). Also, opioid withdrawal in rodents has been reported to be reduced by n-NOS inhibition (see *Neuropsychopharmacol.*, 13, 269–293, 1995).

Neuropathic pain, as defined by the International Association for the Study of Pain (IASP), is pain initiated or caused by a primary lesion or dysfunction in the nervous system and may be associated with either the central or peripheral nervous system. Neuropathic pain can be subcategorized into central and peripheral neuropathic pain corresponding to lesions or dysfunction to the peripheral and central nervous system respectively. In contrast to acute nociceptive pain, which is finite, localized, subsides with healing or removal of the noxious substance, and serves a protective biological function by minimizing the exposure potential of continuing tissue damage, chronic neuropathic pain serves no protective biological function. Thus rather than being a symptom of a disease process it is itself a disease process that can persist long after the initial injury. If chronic pain is inadequately treated, associated symptoms of chronic anxiety, depression, fear, sleeplessness and social impairment may result.

Nociceptive and neuropathic pain are caused by different neurophysiological processes and thus tend to respond to different treatments. Nociceptive pain, whether somatic or visceral in nature, is mediated by A-delta and C-fibres located in skin, bone, vicera etc. Examples of this type of pain include post-operative pain, pain associated with trauma and arthritic pain and can be effectively managed with opioids or NSAIDS. Neuropathic pain is caused by pathological changes such as peripheral or central neuronal sensitization, abonormal somatic and sympathetic interactions, and central sensitization related to damaged inhibitory neuronal function. These abnormal states are manifested in the development of hyperalgesia and allodynia. Hyperalgesia corresponds to augmented pain intensity in response to a normally painful stimulus while allodynia refers to nociceptive response to normally innocuous stimuli, whether due to tactile (touch) or cold. There are many causes of neuropathic pain giving rise to hyperalgesia and allodynia and include major and minor surgery (eg dental surgery, mastectomy), major and minor trauma (eg. spinal cord damage, sports related injuries), loss of limbs (eg. phantom limb pain) neurological disorders (stroke, MS, fibromyalgia), psychiatric and affective disorders, chemically induced injury (eg chemotherapy such as cisplatin and taxol treatment), metabolic disorders (eg. diabetes), viral induced pain (eg. Shingles, HIV associated neuropathy, postherpetic neuraligia from herpes zoster) and mechanical or tactile allodynia associated with migraine. Any disease which can result in nerve damage can give rise to neuropathic pain states.

Early evidence for the role of NO in pain transmission (Meller and Gebhart; Pain, 1993, 52, 127–136) has lead to intensive research into its involvement. Extensive work has shown that nitric oxide synthase is rich in laminae I-III of the dorsal horn of the spinal cord (Dun. et. al. Neuroscience 1993; 54: 845–857), an area known to be involved in pain processing (Willis and Westlund. J. Clin. Neurophysiol. 1997; 14: 2–31) and that NOS is often co-localized with inhibitory GABA-ergic inhibitory neurons (Lian et. al. Neuroscience 1994; 61: 123–132). Physiological studies have support the role of NO in spinal modulation of pain transmission (Przesmycki et. al. Eur. Neuropsycholpharmacol. 1999; 9: 115–121) but it appears to be more involved in thermal evoked pain or changes in sustained nociceptive responses following injury rather than acute nociceptive reflexes (Meller et. al. Eur. J. Pharmacol. 1992; 214: 93–96, Meller and Gebhart; Pain 1993; 52: 127–136, Stanfa et. al.

Brain Res. 1996; 737: 92–98). Recent studies using direct electrochemical measurements of NO in laminae I-III have shown that NO is released only after a titanic burst percutaneous stimulation, characteristic of activation of activation of Aβ and Aδ fibres, but not after single shock low intensity stimulus (Schulte and Millar. Pain 2003; 103:139–150). NO synthesis could be nearly abolished with the NOS inhibitor L-NAME without effect on receptive fields. Burst stimuli are known to produce windup (frequency dependent increase in the excitability of spinal cord neurones) in the dorsal horn which can be attenuated with the application of NOS inhibitors. Activation of C-fibres also produced a rise in NO levels.

Considerable evidence has demonstrated the NO and NOS are involved in the central mechanisms of inflammatory thermal hyperalgesia at the level of the spinal cord (Tao et. al. Neuroscience; 2000; 95: 525–533, Eur. J. Pharmacol. 2000; 392: 141–145, Neuroscience 2002; 112: 439–446, Handy and More Br. J. Pharmacol. 1998; 123:1119–1126, Neuropharmacology, 1998, 37: 37–43). It appears that both spinal nNOS and iNOS mRNA are upregulated during peripheral inflammation (Guhring et. al. J. Neurosci. 2000; 20: 6714–6720, Wu et. al. Exp. Brain. Res. 1998; 118: 457–465, Pain 2001; 94: 47–57) while eNOS expression after carrageenan injection is not (Tao et. al. Neurosci. 2003; 120: 847–854). Studies have shown that nNOS appears to the predominant player in inflammatory hyperalgesia. For instance, the time course and intensity of carrageenan-induced thermal hyperalgesia in iNOS knockout and wild type mice are similar in both early and late phase (secondary component). In addition, intrathecal (spinal) administration of neuronal selective nNOS inhibitor 7-nitroindazole but not eNOS selective L-N-(1-iminoethyl)ornithine, significantly reduced carrageenan-induced thermal hyperalgesia in iNOS knockout mice. It appears that nNOS may compensate for iNOS function and that iNOS is likely sufficient but not essential for late phase of inflammatory mediated thermal hyperalgesia (Tao et. al. 2003; 120: 847–854).

The use of NOS inhibitors in the treatment of disease has been described, for example, in international patent application nos. WO 94/12163, WO 93/13066, WO 94/12165, WO 95/00505, WO 95/09619, WO 95/09621, WO 95/10266, WO 95/11231, WO 95/11014, WO 96/01817 and WO 98/50382, and in European patent application nos. EP 446699, EP 547558, and EP 558468.

NOS inhibitors can be therapeutic in many disorders, but preservation of physiologically important nitric oxide synthase function requires the development of isoform-selective inhibitors.

SUMMARY OF THE INVENTION

It has been found that certain aminobenzothiazole compounds show nitric oxide synthase (NOS) inhibiting activity.

The present invention therefore provides compounds of Formula I, and pharmaceutically acceptable salts, solvates and prodrugs thereof:

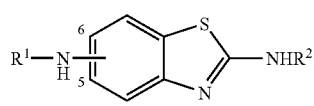

I wherein
$R^1$ is selected from the group consisting of:

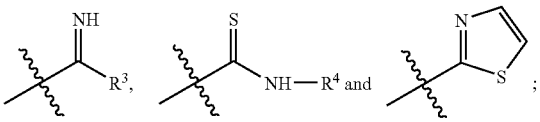

$R^2$ is selected from the group consisting of H,

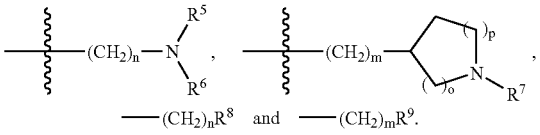

$R^3$ is selected from the group consisting of $C_{1-6}$alkyl, $SC_{1-6}$alkyl, thienyl and furanyl;

$R^4$ is selected from the group consisting of H, $C_{1-6}$alkyl, Ph, C(O)Ph and —C(O)$C_{1-6}$alkyl;

$R^5$ and $R^6$ are independently selected from the group consisting of H and $C_{1-6}$alkyl or together $R^5$ and $R^6$ and the nitrogen to which they are attached form a 3 to 7-membered azacarbocylic ring wherein one of the carbon atoms in the ring may optionally be replaced with O, S, or $NR^7$;

$R^7$ is selected from the group consisting of H, $C_{1-6}$alkyl, Ph, Heteroaryl, $CH_2$Ph, and $CH_2$Heteroaryl, with Ph and Heteroaryl being optionally substituted with 1–3 groups independently selected from the group consisting of $C_{1-4}$alkyl, halo, OH, $OC_{1-4}$alkyl, $NH_2$, $NH(C_{1-4}$alkyl), $N(C_{1-4}$alkyl)($C_{1-4}$alkyl), nitro and cyano;

$R^8$ is selected from the group consisting of H, OH, Ph, naphthyl and heteroaryl, with Ph, naphthyl and heteroaryl being optionally substituted with 1–3 groups independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl;

$R^9$ is $C_{3-7}$cycloalkyl optionally substituted with 1–3 groups independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl and one or two of the carbon atoms in $C_{3-7}$cycloalkyl may optionally be replaced with O or S;

n is 1–6;
m is 0–6;
o is 0–2;
q is 0–6; and the group $R^1NH$— is attached to the 5- or 6-position of the aminobenzothiazole ring, with the proviso that when $R^2$ is H then $R^4$ is not $C_{1-6}$alkyl.

According to another aspect of the present invention, there is provided a pharmaceutical composition comprising a compound of Formula I and a pharmaceutically acceptable carrier or diluent.

Compounds of Formula I, including those wherein $R^4$ is $C_{1-6}$alkyl when $R^2$ is H, have useful NOS inhibiting activity, and therefore are useful in the treatment, or reducing the risk of, diseases or conditions which benefit from an inhibition of NOS activity. Such diseases or conditions include those in which the synthesis or oversynthesis of nitric oxide plays a contributory part. In particular, the compounds of Formula I, including those where $R^4$ is $C_{1-6}$alkyl and the group $R^1NH$— is attached to the 5-position of the aminobenzothiazole ring, exhibit selective inhibition of the neuronal isoform of NOS.

Accordingly, the present invention relates to a method of treating, or reducing the risk of, a disease or condition which benefits from an inhibition of NOS activity comprising administering an effective amount of a compound of Formula I, including those wherein $R^4$ is $C_{1-6}$alkyl when $R^2$ is H, to a cell or animal in need thereof. The invention also includes the use of a compound of Formula I, including those wherein $R^4$ is $C_{1-6}$alkyl when $R^2$ is H, to treat, or reduce the risk of, a disease or condition which benefits from an inhibition of NOS activity. Further, the invention includes the use of a compound of Formula I, including those wherein $R^4$ is $C_{1-6}$alkyl when $R^2$ is H, to prepare a medicament to treat, or reduce the risk of, a disease or condition which benefits from an inhibition of NOS activity.

Examples of diseases and other conditions that may benefit from an inhibition of NOS activity include migraine, inflammatory diseases including reversible obstructive airway diseases (e.g., asthma and adult respiratory distress syndrome (ARDS)), stroke, neurological deficits associated with coronary artery bypass graft (CABG), neuropathic pain, acute and chronic pain, traumatic shock, reperfusion injury, multiple sclerosis, AIDS associated dementia, neurodegenerative diseases, neuron toxicity, Alzheimer's disease, chemical dependencies and addictions (e.g., dependencies on drugs, alcohol and nicotine), epilepsy, anxiety, head trauma, morphine induced tolerance and withdrawal symptoms, acute spinal cord injury, Huntington's disease, Parkinson's disease, glaucoma, macular degeneration, diabetic nephropathy.

In an embodiment of the invention, the conditions are stroke, reperfusion injury, neurodegeneration, head trauma, neurological deficits associated with coronary artery bypass graft (CABG), migraine, neuropathic pain and chronic pain. In a further embodiment of the invention, the condition is neuropathic pain or stroke.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

I. Definitions

Figure 1:
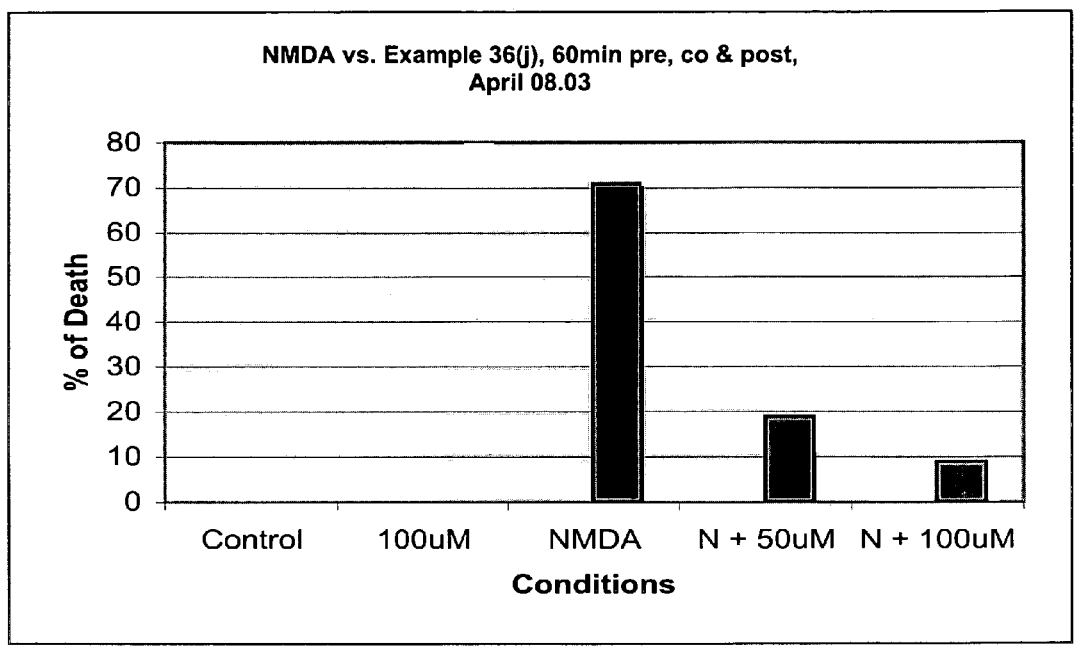
FIG. 1 is a bar graph illustrating the neuroprotection observed during NMDA challenge when rat cortical cells are preincubated with N-{2-[2-(3H-imidazol-4-yl)-ethylamino]-benzothiazol-6-yl}-thiophene-2-carboxamidine for 60 minutes.

The term "$C_{1-4}$alkyl" as used herein means straight and/or branched chain alkyl radicals containing from one to four carbon atoms and includes methyl, ethyl, propyl, isopropyl, t-butyl and the like.

The term "$C_{1-6}$alkyl" as used herein means straight and/or branched chain alkyl radicals containing from one to six carbon atoms and includes methyl, ethyl, propyl, isopropyl, t-butyl, pentyl and the like.

The term "halo" as used herein means halogen and includes chloro, bromo, iodo, fluoro and the like.

The term "Ph" as used herein means phenyl.

The term "3- to 7-membered azacarbocyclic ring" as used herein refers to a saturated carbocycle containing one nitrogen atom and includes pyrrolidine, piperazine, homopiperazine and the like. One of the carbon atoms in the azacarbocyclic ring may optionally be substituted with an oxygen atom, sulfur atom or the group $NR^7$, wherein $R^7$ is as defined in Formula I.

The term "heteroaryl" as used herein refers to mono and bicyclic aromatic rings containing from 5 to 10 atoms of which 1–3 may be a heteroatom or substituted heteroatom selected from the group consisting of O, S, NH and $NC_{1-4}$alkyl. The remaining atoms in the ring are carbon atoms. Examples of heteroaryl groups include, but are not limited to, pyridinyl, imidazolyl, thienyl, furanyl, indolyl, isoquinolinyl, quinolinyl, benzothienyl, benzofuranyl and the like.

The term "$C_{3-7}$cycloalkyl" as used herein refers to saturated carbocylic rings containing from 3 to 7 carbon atoms and includes cyclopropyl, cyclobutyl, cyclopentyl, cyclohexyl and cycloheptyl. One or two of the carbon atoms in the $C_{3-7}$cycloalkyl groups of the invention may optionally be replaced with an O or S atom.

The term "pharmaceutically acceptable" means suitable for or compatible with the treatment of animals, in particular humans.

The term "pharmaceutically acceptable acid addition salt" as used herein means any non-toxic organic or inorganic salt of any base compound of the invention, or any of their intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the invention are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the invention, for laboratory use, or for subsequent conversion to a pharmaceutically acceptable acid addition salt.

The term "solvate" as used herein means a compound of the invention wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term "compound(s) of the invention" as used herein means a compound(s) of Formula I, including those wherein $R^4$ is $C_{1-6}$alkyl when $R^2$ is H, and salts, solvates and prodrugs thereof.

The term an "effective amount" or a "sufficient amount" of an agent as used herein is that amount sufficient to effect beneficial or desired results, including clinical results, and, as such, an "effective amount" depends upon the context in which it is being applied. For example, in the context of administering an agent that is an inhibitor of NOS, an effective amount of an agent is, for example, an amount sufficient to achieve such a reduction in NOS activity as compared to the response obtained without administration of the agent.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

To "inhibit" or "suppress" or "reduce" a function or activity, such as NOS activity, is to reduce the function or activity when compared to otherwise same conditions except for a condition or parameter of interest, or alternatively, as compared to another condition.

The term "animal" as used herein includes all members of the animal kingdom including human. The animal is preferably a human.

The term "a cell" as used herein includes a plurality of cells. Administering a compound to a cell includes in vivo, ex vivo and in vitro treatment.

II. Compounds of the Invention

Novel compounds showing inhibition of NOS are provided. As such, these compounds are useful for treating or reducing the risk of diseases or disorders which benefit from an inhibition of NOS. For example, the compounds of the invention are useful as neuroprotectants for treating conditions such as stroke.

The present invention therefore provides compounds of Formula I, and pharmaceutically acceptable salts, solvates and prodrugs thereof:

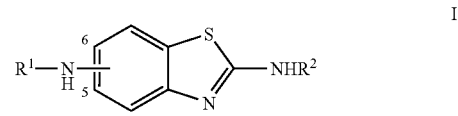

wherein
$R^1$ is selected from the group consisting of:

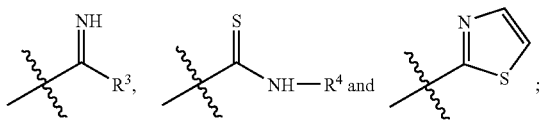

$R^2$ is selected from the group consisting of H,

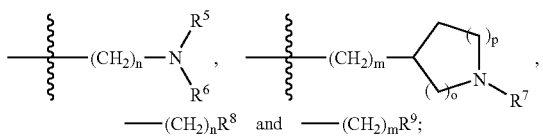

$R^3$ is selected from the group consisting of $C_{1-6}$alkyl, $SC_{1-6}$alkyl, thienyl and furanyl;

$R^4$ is selected from the group consisting of H, $C_{1-6}$alkyl, Ph, C(O)Ph and —C(O)$C_{1-6}$alkyl;

$R^5$ and $R^6$ are independently selected from the group consisting of H and $C_{1-6}$alkyl or together $R^5$ and $R^6$ and the nitrogen to which they are attached form a 3 to 7-membered azacarbocylic ring wherein one of the carbon atoms in the ring may optionally be replaced with O, S, or $NR^7$;

$R^7$ is selected from the group consisting of H, $C_{1-6}$alkyl, Ph, Heteroaryl, $CH_2$Ph, and $CH_2$Heteroaryl, with Ph and Heteroaryl being optionally substituted with 1–3 groups independently selected from the group consisting of $C_{1-4}$alkyl, halo, OH, $OC_{1-4}$alkyl, $NH_2$, $NH(C_{1-4}$alkyl), $N(C_{1-4}$alkyl)($C_{1-4}$alkyl), nitro and cyano;

$R^8$ is selected from the group consisting of H, OH, Ph, naphthyl and heteroaryl, with Ph, naphthyl and heteroaryl being optionally substituted with 1–3 groups independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl;

$R^9$ is $C_{3-7}$cycloalkyl optionally substituted with 1–3 groups independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl and one or two of the carbon atoms in $C_{3-7}$cycloalkyl may optionally be replaced with O or S;

n is 1–6;
m is 0–6;

o is 0–2;

p is 1–2; and the group R$^1$NH— is attached to the 5- or 6-position of the aminobenzothiazole ring, with the proviso that when R$^2$ is H then R$^4$ is not C$_{1-6}$alkyl.

The present invention includes compounds of Formula I wherein R$^1$ is selected from the group consisting of:

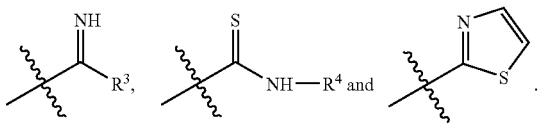

Further, when R$^1$ is

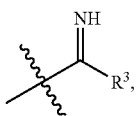

R$^3$ is selected from the group consisting of C$_{1-6}$alkyl, SC$_{1-6}$alkyl, thienyl and furanyl. In embodiments of the present invention, R$^3$ is selected from the group consisting of C$_{1-2}$alkyl, SC$_{1-4}$alkyl and thienyl. In further embodiments of the present invention, R$^3$ is selected from the group consisting of SC$_{1-2}$alkyl and thienyl. Alternatively, when R$^1$ is

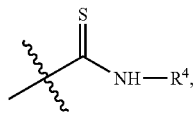

R$^4$ is selected from the group consisting of H, C$_{1-6}$alkyl, Ph, C(O)Ph and —C(O)C$_{1-6}$alkyl. In embodiments of the invention, R$^4$ is selected from the group consisting of H, C$_{1-4}$alkyl, Ph, C(O)Ph and —C(O)C$_{1-4}$alkyl. In further embodiments of the invention, R$^4$ is selected from the group consisting of H, and C(O)Ph.

In the present invention, the compounds of Formula I include those in which R$^2$ is selected from the group consisting of H,

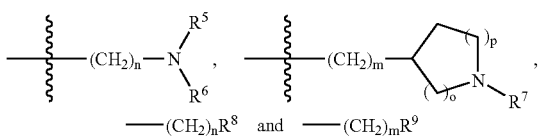

In embodiments of the present invention, when R$^2$ is

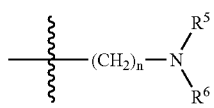

in the compounds of Formula I, R$^5$ and R$^6$ are independently selected from the group consisting of H and C$_{1-6}$alkyl or together R$^5$ and R$^6$ and the nitrogen to which they are attached form a 3 to 7-membered azacarbocyclic ring wherein one of the carbon atoms in the ring may optionally be replaced with O, S, or NR$^7$. In embodiments of the invention, R$^5$ and R$^6$ are independently selected from a group consisting of H and C$_{1-4}$alkyl or together R$^5$ and R$^6$ and the nitrogen to which they are attached form a 4 to 6-membered azacarbocyclic ring wherein one of the carbon atoms in the ring may optionally be replaced with O, S, or NR$^7$. In further embodiments, R$^5$ and R$^6$ are independently selected from a group consisting of H and CH$_3$ or together R$^5$ and R$^6$ and the nitrogen to which they are attached form a 5 to 6-membered azacarbocyclic ring in which one of the carbon atoms in the ring may optionally be replaced with O, S or NR$^7$.

The compounds Formula I include those in which R$^7$ is selected from the group consisting of H, C$_{1-6}$alkyl, Ph, Heteroaryl, CH$_2$Ph, and CH$_2$Heteroaryl, with Ph and Heteroaryl being optionally substituted with 1–3 groups independently selected from the group consisting of C$_{1-4}$alkyl, halo, OH, OC$_{1-4}$alkyl, NH$_2$, NH(C$_{1-4}$alkyl), N(C$_{1-4}$alkyl)(C$_{1-4}$alkyl), nitro and cyano. In embodiments of the invention, R$^7$ is selected from H, C$_{1-4}$alkyl, Ph, Heteroaryl, CH$_2$Ph, and CH$_2$Heteroaryl, with Ph and Heteroaryl being optionally substituted with 1–2 groups independently selected from the group consisting of C$_{1-4}$alkyl, halo, OH, OC$_{1-4}$alkyl, NH$_2$, NH(C$_{1-4}$alkyl), N(C$_{1-4}$alkyl)(C$_{1-4}$alkyl), nitro and cyano. In further embodiments, R$^7$ is selected from H, C$_{1-4}$alkyl, Ph, Heteroaryl, CH$_2$Ph, and CH$_2$Heteroaryl, with Ph and Heteroaryl being optionally substituted with 1 group independently selected from the group consisting of C$_{1-4}$alkyl, halo, OH, OC$_{1-4}$alkyl, NH$_2$, NH(C$_{1-4}$alkyl), N(C$_{1-4}$alkyl)(C$_{1-4}$alkyl), nitro and cyano. In still further embodiments, R$^7$ is selected from H, C$_{1-4}$alkyl Ph, Heteroaryl, and CH$_2$Ph, with Ph being optionally substituted with 1 groups independently selected from the group consisting of C$_{1-4}$alkyl, halo, OH, OC$_{1-4}$alkyl, NH$_2$, NH(C$_{1-4}$alkyl), N(C$_{1-4}$alkyl)(C$_{1-4}$alkyl), nitro and cyano. In further embodiments of the invention, R$^7$ is selected from methyl and CH$_2$Ph.

When R$^2$ is —(CH$_2$)$_n$R$^8$, R$^8$ is selected from the group consisting of H, OH, Ph, naphthyl and heteroaryl, with Ph, naphthyl and heteroaryl being optionally substituted with 1–3 groups independently selected from the group consisting of C$_{1-4}$alkyl, halo, NH$_2$, NH(C$_{1-4}$alkyl), N(C$_{1-4}$alkyl)(C$_{1-4}$alkyl), nitro, cyano, OH and OC$_{1-4}$alkyl. In embodiments of the invention, R$^8$ is selected from the group consisting of H, OH, Ph and heteroaryl, with Ph and heteroaryl being optionally substituted with 1–2 groups independently selected from the group consisting of C$_{1-4}$alkyl, halo, NH$_2$, NH(C$_{1-4}$alkyl), N(C$_{1-4}$alkyl)(C$_{1-4}$alkyl), nitro, cyano, OH and OC$_{1-4}$alkyl. In further embodiments, R$^8$ is selected from the group consisting of H OH, Ph, and heteroaryl, with Ph and heteroaryl being optionally substituted with 1–2 groups independently selected from the group consisting of C$_{1-4}$alkyl, halo, NH$_2$, NH(C$_{1-4}$alkyl), N(C$_{1-4}$alkyl)(C$_{1-4}$alkyl), nitro, cyano, OH and OC$_{1-4}$alkyl. In still further embodiments, heteroaryl is a 5 or 6 membered aromatic ring. In even further embodiments, heteroaryl is selected from pyridyl, imidazolyl, thienyl and furanyl.

When R$^2$ is —(CH$^2$)$_q$R$^9$, R$^9$ is C$_{3-7}$cycloalkyl optionally substituted with 1–3 groups independently selected from the group consisting of C$_{1-4}$alkyl, halo, NH$_2$, NH(C$_{1-4}$alkyl), N(C$_{1-4}$alkyl)(C$_{1-4}$alkyl), nitro, cyano, OH and OC$_{1-4}$alkyl and one or two of the carbon atoms in C$_{3-7}$cycloalkyl may optionally be replaced with O or S. In embodiments of the invention, $R^9$ is $C_{3-7}$cycloalkyl optionally substituted with 1–2 groups independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl and one of the carbon atoms in $C_{3-7}$cycloalkyl may optionally be replaced with O or S. In further embodiments $R^9$ is $C_{5-7}$cycloalkyl optionally substituted with 1 group independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl and one of the carbon atoms in $C_{3-7}$cycloalkyl may optionally be replaced with O or S. In still further embodiments, $R^9$ is $C_{5-7}$cycloalkyl herein one of the carbon atoms in $C_{3-7}$cycloalkyl may optionally be replaced with O. In even further embodiments, $R^9$ is selected from cyclopropyl, cyclobutyl, cyclopentyl, cyclohexyl and cycloheptyl, tetrahydropyranyl or tetrahydrofuran.

The present invention includes compounds of Formula I wherein n is 1–6. In embodiments of the invention, n is 1–4. In further embodiments, n is 2–3. In still further embodiments, n is 2.

The present invention also includes compounds of Formula I, wherein m is 0–6. In embodiments of the invention, m is 0–4. In further embodiments, m is 0–2.

Compounds of Formula I, further include those wherein o is 1–2. In embodiments, o is 1. Compounds of Formula I, further include those wherein p is 1–2. In embodiments of the invention, both o and p are 1 (to provide a pyrrolidinyl ring). In still further embodiments, both o and p are 2 (to provide a piperidinyl ring).

In an embodiment of the present invention, when $R^1$ is

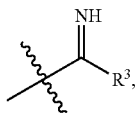

the compounds of Formula I include those wherein $R^3$ is selected from the group consisting of $SC_{1-4}$alkyl and thienyl, attached to the 5- or 6-position of the aminobenzothiazole ring.

In a further embodiment of the present invention, when $R^1$ is

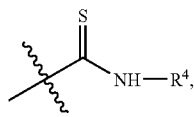

$R^4$ is selected from the group consisting of H and C(O)Ph, attached to the 5- or 6-position of the aminobenzothiazole ring.

In yet another embodiment of the present invention, $R^1$ is

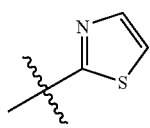

attached to the 5- or 6-position of the aminobenzothiazole ring.

In specific embodiments of the present invention, the compounds of Formula I include:

N-(2-Amino-benzothiazol-6-yl)-2-methylthiocarboximidamide;
N-(2-Amino-benzothiazol-6-yl)-2-ethylthiocarboximidamide;
N-(2-Amino-benzothiazol-6-yl)-2-propylthiocarboximidamide;
N-(2-Amino-benzothiazol-6-yl)-2-isopropylthiocarboximidamide;
N-(2-Amino-benzothiazol-6-yl)-2-methylcarboximidamide;
N-(2-Amino-benzothiazol-6-yl)-2-thiophenecarboximidamide;
N-[2-(2-pyrrolidin-1-ylethylamino)-benzothiazol-6-yl]-2-thiophenecarboximidamide;
1-(2-Amino-benzothiazol-5-yl)-3-benzoyl-thiourea;
1-(2-Amino-benzothiazol-5-yl)-3-ethyl-thiourea;
N-(2-Amino-benzothiazol-5-yl)-thiophene-2-carboxamidine;
N5-Thiazol-2-yl-benzothiazole-2,5-diamine;
(2-Amino-benzothiazol-5-yl)-thiourea;
N-[2-(Tetrahydro-pyran-4-ylamino)-benzothiazol-6-yl]-thiophene-2-carboxamidine;
N-{2-[2-(4-Bromo-phenyl)-ethylamino]-benzothiazol-6-yl}-thiophene-2-carboxamidine;
N-[2-(2-Pyridin-2-yl-ethylamino)-benzothiazol-6-yl]-thiophene-2-carboxamidine;
N-[2-(1-Benzyl-piperidin-4-ylamino)-benzothiazol-6-yl]-thiophene-2-carboxamidine;
N-{2-[2-(3H-Imidazol-4-yl)-ethylamino]-benzothiazol-6-yl}-thiophene-2-carboxamidine;
N-[2-(2-Morpholin-4-yl-ethylamino)-benzothiazol-6-yl]-thiophene-2-carboxamidine;
N-[2-(2-Dimethylamino-ethylamino)-benzothiazol-5-yl]-thiophene-2-carboxamidine;
N-{2-[2-(1-Methyl-pyrrolidin-2-yl)-ethylamino]-benzothiazol-5-yl}-thiophene-2-carboxamidine;
N-{2-[2-(3-Chloro-phenyl)-ethylamino]-benzothiazol-6-yl}-thiophene-2-carboxamidine;
N-[2-(4-Hydroxy-butylamino)-benzothiazol-6-yl]-thiophene-2-carboxamidine;
N-[2-(3-Imidazol-1-yl-propylamino)-benzothiazol-6-yl]-thiophene-2-carboxamidine;
N2-(1-Benzyl-piperidin-4-yl)-N-6-thiazol-2-yl-benzothiazole-2,6-diamine;
1-Benzoyl-3-{2-[2-(4-bromo-phenyl)-ethylamino]-benzothiazol-6-yl}-thiourea;
{2-[2-(4-Bromo-phenyl)-ethylamino]-benzothiazol-6-yl}-thiourea; and
1-{2-[2-(4-Bromo-phenyl)-ethylamino]-benzothiazol-6-yl}-2-ethyl-isothiourea.

Where the compounds of invention possess asymmetric centre, for example, when $R^2$ is

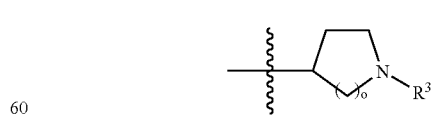

and o is other than 2, they may exist as enantiomers. It is to be understood that all such enantiomers and mixtures thereof in any proportion are encompassed within the scope of the present invention. Further, the invention extends to all tautomers of the compounds of the present invention.

As to any of the above groups that contain one or more substituents, it is understood, of course, that such groups do not contain any substitution or substitution patterns which are sterically impractical and/or synthetically non-feasible.

III. Methods of Preparing Compounds of the Invention

In accordance with another aspect of the present invention, the compounds of the invention can be prepared by processes analogous to those established in the art. Therefore, compounds of the invention may be prepared, for example, by the reaction sequences shown in Schemes 1–7.

Compounds of the invention, wherein $R^1$ is

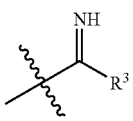

and $R^3$ is $SC_{1-6}$alkyl, may be prepared, for example, by reacting compounds of the invention, wherein $R^1$ is

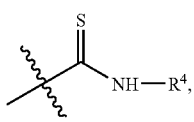

$R^4$ is H and $R^2$ is as defined in Formula I, with a reagent of Formula B, wherein LG is a suitable leaving group such as a halogen, preferably iodo, under standard alkylating conditions as shown in Scheme 1.

Scheme 1

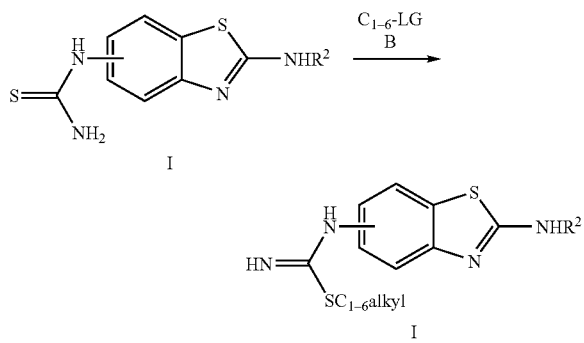

Compounds of the invention, wherein $R^1$ is

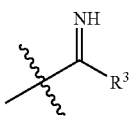

and $R^3$ is thienyl, furanyl and $C_{1-6}$alkyl, may be prepared, for example, as shown in Scheme 2. Therefore reagents of Formula C, wherein $R^2$ is as defined in Formula I, may be reacted with reagents of Formula D or E, wherein Q may be, for example phenyl or naphthylmethyl and X is O or S, in an alcohol solvent such as ethanol, to provide compounds of the invention, wherein $R^1$ is

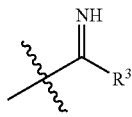

and $R^3$ is thienyl, furanyl and $C_{1-6}$alkyl.

Scheme 2

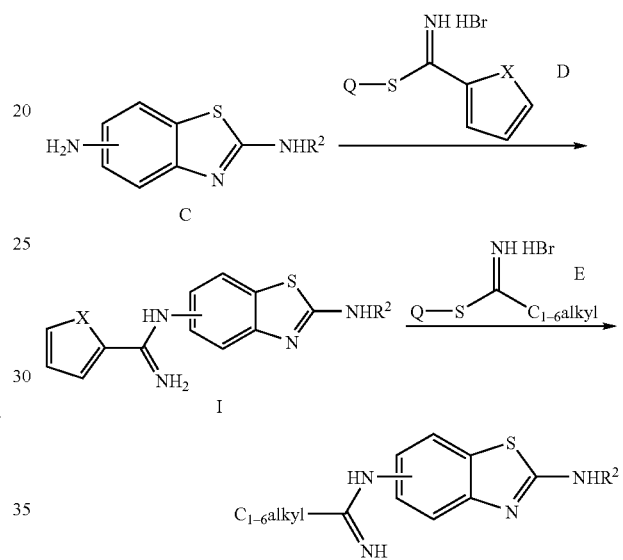

Compounds of the invention, wherein $R^1$ is

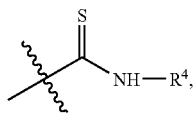

wherein $R^4$ is $C_{1-6}$alkyl, Ph, C(O)Ph and —C(O)$C_{1-6}$alkyl, and $R^2$ is as defined in Formula I, may be prepared from a reagent of Formula C, wherein $R^2$ is as defined in Formula I, for example, as shown in Scheme 3. Therefore, reagents of Formula C are reacted with a reagent of Formula F, wherein $R^4$ is $C_{1-6}$alkyl, Ph, C(O)Ph and —C(O)$C_{1-6}$alkyl in an inert solvent such as tetrahydrofuran, suitably at ambient temperature or with heating. Compounds of the invention, wherein $R^1$ is

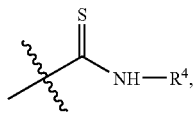

$R^4$ is H, and $R^2$ is as defined in Formula I, may be prepared by hydrolysis of a compound of the invention, wherein $R^1$ is

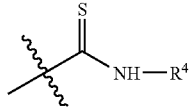

and $R^4$ is C(O)Ph using standard conditions (for example aqueous sodium hydroxide in tetrahydrofuran) as shown in Scheme 3.

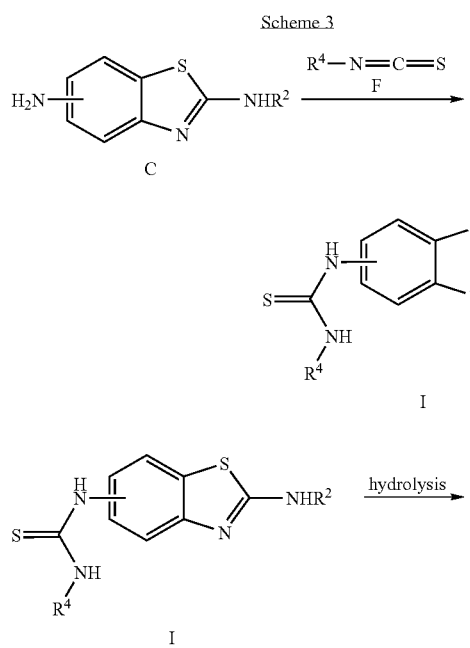

$R^4$ = C(O)Ph

Compounds of the invention, wherein $R^1$ is

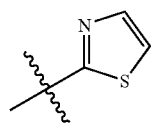

and $R^2$ is as defined in Formula I, may be prepared, for example, by reacting a compound of the invention, wherein $R^1$ is

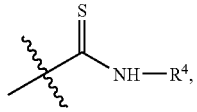

$R^4$ is H, and $R^2$ is as defined in Formula I, with chloroacetaldehyde in a polar solvent, such as ethanol, suitably under refluxing conditions, as shown in Scheme 4.

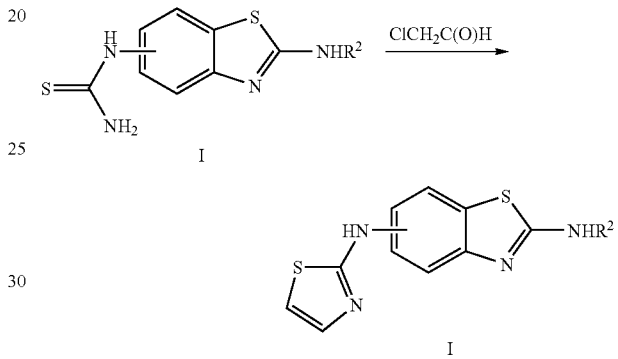

Reagents of Formula C, wherein $R^2$ is as defined in Formula I, may be prepared, for example, by reducing the nitro group of a reagent of Formula G, wherein $R^2$ is as defined in Formula I, under standard conditions as shown in Scheme 5. Standard reduction conditions may be, for example, $SnCl_2$ in a polar solvent, such as ethanol, at refluxing temperatures.

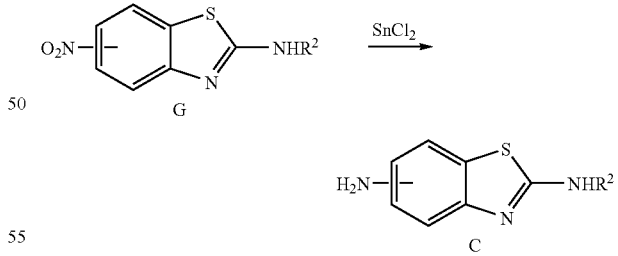

Reagents of Formula G, wherein $R^2$ is selected from the group consisting of

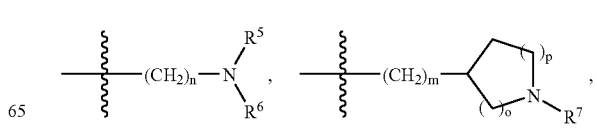

—$(CH_2)_nR^8$ and —$(CH_2)_mR^9$ and $R^5$—$R^9$ and n, m, o and p are as defined in Formula I, may be prepared, for example, be treating a reagent of Formula H with a reagent of Formula J, wherein $R^2$ is selected from the group consisting of

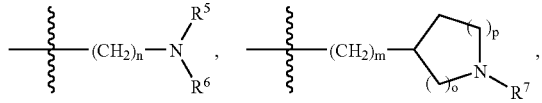

—$(CH_2)_nR^8$ and —$(CH_2)_mR^9$ and $R^5$—$R^9$ and n, m, o and p are as defined in Formula I, under standard alkylating conditions as shown in Scheme 6. Conditions to effect the alkylation of reagents J with reagents H may include, for example, heating reagents J and H together with or without a solvent, optionally in the presence of a suitable base.

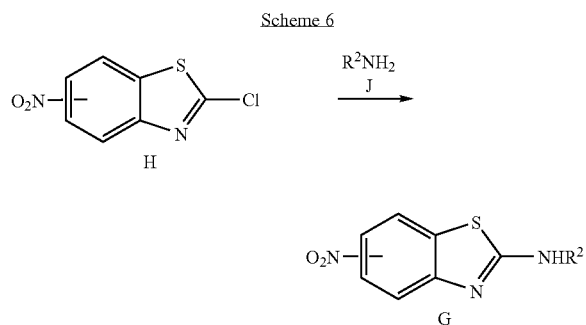

Reagents of Formula G, wherein $R^2$ is H, reagents of Formula H and reagents of Formula J, wherein $R^2$ is selected from the group consisting of

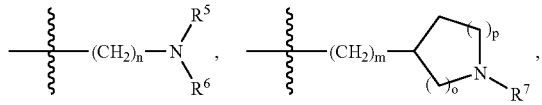

—$(CH_2)_nR^8$ and —$(CH_2)_mR^9$ and $R^5$—$R^9$ and n, m, o and p are as defined in Formula I, are commercially available or may be prepared using standard methodologies known to a person skilled in the art (see for example, Examples 14–16 herein below).

An alternate route to reagents of Formula C, wherein $R^2$ is selected from the group consisting of

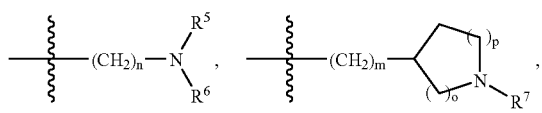

—$(CH_2)_nR^8$ and —$(CH_2)_mR^9$ and $R^5$—$R^9$ and n, m, o and p are as defined in Formula I, involves the reaction of a reagent of Formula K, with a reagent of Formula L, wherein $R^2$ is selected from the group consisting of

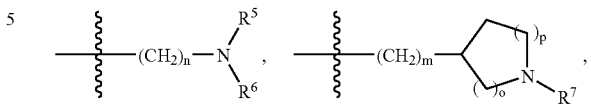

—$(CH_2)_nR^8$ and —$(CH_2)_mR^9$ and $R^5$—$R^9$ and n, m, o and p are as defined in Formula I and LG is a suitable leaving group, such as halo, suitably chloro, under standard alkylation conditions as shown in Scheme 7. The resulting nitro compound may be reduced to the corresponding amino compound C as described above. Reagents of Formula K are either commercially available or may be prepared using standard methodologies.

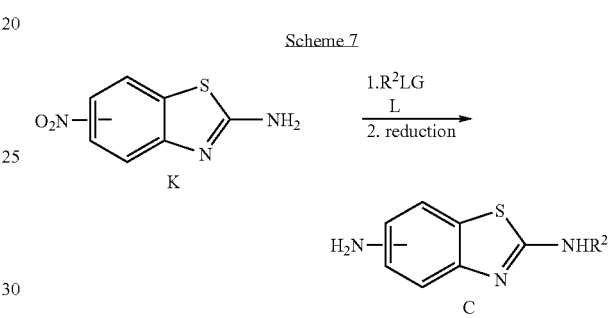

Reagents of Formula D and E are either commercially available or may be prepared by reacting the corresponding cyano compounds with a thiol, Q—SH, wherein Q may be, for example phenyl or naphthylmethyl, followed by quenching with HBr, as shown in Scheme 8.

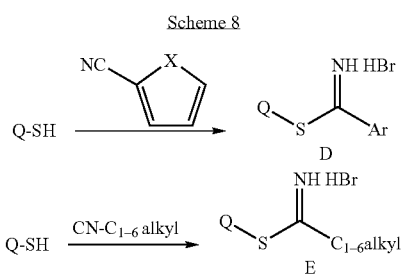

In some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 1991.

The compounds of the invention, and intermediates in the preparation of the compounds of the invention, may be isolated from their reaction mixtures and purified (if necessary) using conventional techniques, including, for example, extraction, chromatography, distillation and recrystallization.

The formation of a desired compound salt is achieved using standard techniques. For example, the neutral compound is treated with an acid or base in a suitable solvent and the formed salt is isolated by filtration, extraction or any other suitable method.

The formation of solvates of the compounds of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

Preparation of an optical isomer of a compound of the invention may be performed by reaction of the appropriate optically active starting materials under reaction conditions which will not cause racemization. Alternatively, the individual enantiomers may be isolated by separation of a racemic mixture using standard techniques, for example fractional crystallization or HPLC.

Prodrugs of the compounds of the invention may be conventional esters formed with an available amino group. For example, when $R^2$ is H in a compound of the invention, it may be acylated using an activated acid in the presence of a base, and optionally, in inert solvent (e.g. an acid chloride in pyridine). Some common esters which have been utilized as prodrugs are phenyl esters, aliphatic ($C_8$–$C_{24}$) esters, acyloxymethyl esters, carbamates and amino acid esters.

A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodo may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine)palladium (0) in an inert solvent, such as dioxane, and at elevated temperatures, suitably 50–100° C.

IV. Uses

As hereinbefore mentioned, novel compounds having the general Formula I have been prepared. Accordingly, the present invention includes all uses of the compounds of Formula I, including their use in therapeutic methods and compositions for inhibiting NOS activity, their use in diagnostic assays and their use as research tools.

The compounds of the invention, i.e. compounds of Formula I, including those wherein $R^4$ is $C_{1-6}$alkyl when $R^2$ is H, have useful NOS inhibiting activity, and therefore are useful in the treatment, or reducing the risk of, diseases or conditions which benefit from an inhibition of NOS activity. Such diseases or conditions include those in which the synthesis or oversynthesis of nitric oxide plays a contributory part.

Accordingly, the present invention relates to a method of treating, or reducing the risk of, a disease or condition which benefits from an inhibition of NOS activity comprising administering an effective amount of a compound of Formula I, including those wherein $R^4$ is $C_{1-6}$alkyl when $R^2$ is H, to a cell or animal in need thereof. The invention also includes the use of a compound of Formula I, including those wherein $R^4$ is $C_{1-6}$alkyl when $R^2$ is H, to treat, or reduce the risk of, a disease or condition which benefits from an inhibition of NOS activity. Further, the invention includes the use of a compound of Formula I, including those wherein $R^4$ is $C_{1-6}$alkyl when $R^2$ is H, to prepare a medicament to treat, or reduce the risk of, a disease or condition which benefits from an inhibition of NOS activity.

Examples of diseases and other conditions that may benefit from an inhibition of NOS activity include migraine, inflammatory diseases including reversible obstructive airway diseases (e.g., asthma and adult respiratory distress syndrome (ARDS)), stroke, neurological deficits associated with coronary artery bypass graft (CABG), neuropathic pain, acute and chronic pain, traumatic shock, reperfusion injury, multiple sclerosis, AIDS associated dementia, neurodegenerative diseases, neuron toxicity, Alzheimer's disease, chemical dependencies and addictions (e.g., dependencies on drugs, alcohol and nicotine), epilepsy, anxiety, head trauma, morphine induced tolerance and withdrawal symptoms, acute spinal cord injury, Huntington's disease, Parkinson's disease, glaucoma, macular degeneration, diabetic nephropathy.

In an embodiment of the inventio, the conditions are stroke, reperfusion injury, neurodegeneration, head trauma, neurological deficits associated with coronary artery bypass graft (CABG), migraine, neuropathic pain and chronic pain.

The compounds of the invention, i.e. compounds of Formula I, including those wherein $R^4$ is $C_{1-6}$alkyl when $R^2$ is H, in particular exhibit selective inhibition of the neuronal isoform of NOS. As herein before mentioned, the NO produced by the nNOS isoform during cerebral ischemia may contribute to the initial metabolic deterioration of the ischemic penumbra, resulting in larger infarcts. The present invention therefore provides a method for treating and or reducing the risk of stroke comprising administering an effective amount of a compound of Formula I, including those wherein $R^4$ is $C_{1-6}$alkyl when $R^2$ is H, to a cell or an animal in need thereof. Further, there is provided a use of a compound of Formula I, including those wherein $R^4$ is $C_{1-6}$alkyl when $R^2$ is H, to treat stroke as well as a use of a compound of Formula I, including those wherein $R^4$ is $C_{1-6}$alkyl when $R^2$ is H, to prepare a medicament to treat stroke.

In an further embodiment of the invention, there is provided a method of treating or preventing neuropathic pain comprising administering an effective amount of a compound of Formula I, including those wherein R4 is $C_{1-6}$alkyl when $R^2$ is H, to a cell or an animal in need thereof.

Compounds may be examined for their efficacy in preferentially inhibiting nNOS and/or iNOS and/or eNOS by a person skilled in the art using the methods described in Example 43, herein below. Further, the compounds of the invention may be tested in standard assays for neuroprotectants (see Example 44 and reference cited therein), in particular for stroke (see for example, *Am. J. Physiol.,* 268, R286 1995) or in standard assays for neuropathic pain (see Example 45 and references cited therein).

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent or carrier.

The compounds of the invention may be used in the form of the free base, in the form of salts, solvates and as prodrugs. All forms are within the scope of the invention.

In accordance with the methods of the invention, the described compounds or salts, solvates or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990—18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or pectin and glycerine. Compositions for rectal administration are conveniently in the form of suppositories containing a conventional suppository base such as cocoa butter.

The compounds of the invention may be administered to an animal alone or in combination with pharmaceutically acceptable carriers, as noted above, the proportion of which is determined by the solubility and chemical nature of the compound, chosen route of administration and standard pharmaceutical practice.

The dosage of the compounds of the invention, and/or compositions comprising a compound of the invention, can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of between 1 mg and 2000 mg (measured as the solid form).

The compounds of the invention can be used alone or in combination with other agents that have NOS activity or in combination with other types of treatment (which may or may not inhibit NOS) to the treat, prevent and/or reduce the risk of stroke or other disorders that benefit from NOS inhibition.

In addition to the above-mentioned therapeutic uses, the compounds of the invention are also useful in diagnostic assays, screening assays and as research tools.

In diagnostic assays the compounds of the invention may be useful in identifying or detecting NOS activity. In such an embodiment, the compounds of the invention may be radiolabelled (as hereinbefore described) and contacted with a population of cells. The presence of the radiolabel on the cells may indicate NOS activity.

In screening assays, the compounds of the invention may be used to identify other compounds that inhibit NOS. As research tools, the compounds of the invention may be used in enzyme assays and assays to study the localization of NOS activity. Such information may be used, for example, for diagnosing or monitoring disease states or progression. In such assays, the compounds of the invention may also be radiolabelled.

The following non-limiting examples are illustrative of the present invention:

EXAMPLES

Example 1

Benzothiazole-2,6-diamine

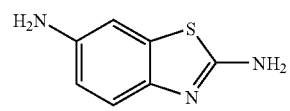

A mixture of 6-nitro-benzothiazol-2-ylamine (1.0 g, 5.12 mmol) and $SnCl_2$ (4.86 g, 25.6 mmol) in 15 mL ethanol (denatured) was heated at reflux for 1 hour. The mixture was concentrated and partitioned between 100 mL $CH_2Cl_2$ and 50 mL 1.0 N NaOH. The organic layer was separated and the aqueous layer was extracted with 2×100 mL of CH$_2$Cl$_2$. The combined organic fractions were dried over MgSO$_4$, filtered and evaporated to give a yellow solid. This was washed with a 1:1 mixture of Et$_2$O and hexanes. Yield: 50%; $^1$H-NMR (acetone-d$_6$): δ 7.14 (d, 1H, J=8.8 Hz); 6.92 (d, 1H, J=1.9 Hz); 6.62 (dd, 1H, J=1.9, 8.5 Hz).

Example 2

1-(2-Amino-benzothiazol-6-yl)-3-benzoylthiourea

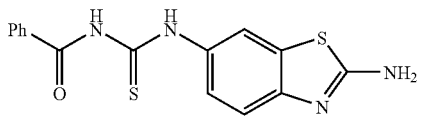

Benzoylisothiocyanate (0.12 mL, 0.91 mmol) was added dropwise to a solution of benzothiazole-2,6-diamine (Example 1, 150 mg, 0.91 mmol) in 10 mL of THF at room temperature. The mixture was stirred at room temperature for 7 hours and then concentrated. The residue was washed with a 1:1 mixture of Et2O and hexanes. Yield: 97.3%, $^1$H-NMR (DMSO-d$_6$): δ 12.65 (s, 1H); 11.55 (s, 1H); 8.00 (m, 3H); 7.60 (m, 5H); 7.38 (m, 2H).

Example 3

1-(2-Amino-benzothiazol-6-yl)thiourea

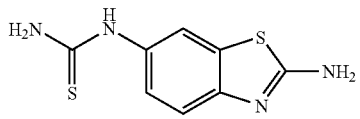

A suspension of 1-(2-amino-benzothiazol-6-yl)-3-benzoyl-thiourea (Example 2, 0.2 g, 0.61 mmol) and 2.0 N NaOH (0.67 mL, 1.34 mmol) in 10 mL of THF was heated at reflux for 4 hours. Upon cooling, a yellow solid precipitated which was filtered. Yield: 66.5%, $^1$H-NMR (DMSO-d$_6$): δ 9.55 (s, 1H); 7.64 (d, 1H, J=1.8 Hz); 7.44 (s, 2H); 7.27 (m, 2H); 7.03 (dd, 1H, J=8.0, 2.0 Hz).

Example 4

N-(2-Amino-benzothiazol-6-yl)-2-methylthiocarbox-imidamide

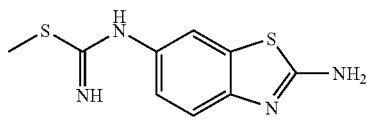

Methyl iodide (19.4 μL, 0.312 mmol) was added to a solution of 1-(2-amino-benzothiazol-6-yl)thiourea (Example 3, 50 mg, 0.312 mmol) in 2 mL of DMF. To this solution was added K$_2$CO$_3$ (129 mg, 0.936 mmol). The suspension was stirred at room temperature for 22 hours. The reaction mixture was diluted with 20 mL of CH$_2$Cl$_2$ and treated with 5 mL of H2O. The organic layer was concentrated and concentrated to give a yellow solid which was subjected to silica gel column chromatography (10% MeOH:90% CH$_2$Cl$_2$). This product was then dissolved in 2 mL MeOH and treated with 0.5 mL of a 2M HCl aqueous solution. After 30 minutes at room temperature, the solvent was evaporated to give a cream-colored solid. Yield: 35%, $^1$H-NMR(D$_2$O): δ 7.80 (d, 1H, J=2.0 Hz); 7.62 (d, 1H, J=8.7 Hz); 7.48 (dd, 1H, J=7.0, 2.2 Hz); 3.35 (s, 3H).

Example 5

N-(2-Amino-benzothiazol-6-yl)-2-ethylthiocarbox-imidamide

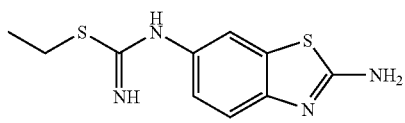

Ethyl iodide (25 μL, 0.312 mmol) was added to a solution of 1-(2-amino-benzothiazol-6-yl)thiourea (Example 3, 50 mg, 0.312 mmol) in 2.5 mL DMF. To this solution was added K$_2$CO$_3$ (129 mg, 0.936 mmol). The suspension was stirred at room temperature for 22 hours. The reaction mixture was diluted with 20 mL of CH$_2$Cl$_2$ and treated with 5 mL of H$_2$O. The organic layer was concentrated and concentrated to give a yellow solid that was subjected to silica gel column chromatography (10% MeOH:90% CH$_2$Cl$_2$). This product was then dissolved in 2 mL of MeOH and treated with 0.5 mL of a 2M HCl aqueous solution. After 30 minutes at room temperature, the solvent was evaporated to give a white solid. Yield: 22%, $^1$H-NMR (D$_2$O): δ 7.86 (d, 1H, J=1.7 Hz); 7.78 (d, 1H, J=8.8 Hz); 7.54 (dd, 1H, J=7.0, 1.9 Hz); 3.32 (q, 2H, J=7.32 Hz); 1.50 (t, 3H, J=7.3 Hz).

Example 6

N-(2-Amino-benzothiazol-6-yl)-2-propylthiocarbox-imidamide

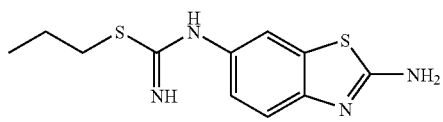

A mixture of 1-(2-amino-berizothiazol-6-yl)thiourea (Example 3, 50 mg, 0.312 mmol), propyl iodide (30.4 μl, 0.312 mmol), and K$_2$CO$_3$ (129 mg, 0.936 mmol) in 2.5 mL of DMF was stirred at room temperature for 24 hours. The mixture was diluted with 20 mL of CH$_2$Cl$_2$ and filtered. The solvent was removed to give a yellow liquid. Toluene was added and a precipitate formed. The precipitate was filtered and dried under vacuo. Yield: 40%, $^1$H-NMR (CD$_3$OD): δ 7.56 (d, 1H, J=2.4 Hz); 7.39 (d, 1H, J=8.8 Hz); 7.11 (dd, 1H, J=6.0, 2.9 Hz); 3.32 (t, 2H, J=7.4 Hz); 1.85 (q, 2H, J=7.3 Hz); 1.10 (t, 3H, J=7.3 Hz).

Example 7

N-(2-Amino-benzothiazol-6-yl)-2-isopropylthiocarboximidamide

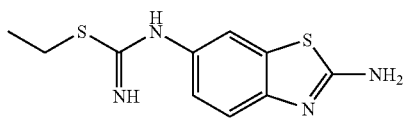

A mixture of 1-(2-amino-benzothiazol-6-yl)thiourea (Example 3, 50 mg, 0.312 mmol), isopropyl iodide (31 μl, 0.312 mmol), and $K_2CO_3$ (129 mg, 0.936 mmol) in 2.5 mL of DMF was stirred at room temperature for 75 hours. The mixture was diluted with 20 mL of $CH_2Cl_2$ and filtered. The solvent was removed to give a yellow solid which was subjected to silica gel column chromatography (5% MeOH: 95% $CH_2Cl_2$).). This product was then dissolved in 2 mL of MeOH and treated with 0.5 mL of a 2M HCl aqueous solution. The solution was then partitioned between 10 mL of $Et_2O$ and 5 mL of $H_2O$. The aqueous layer was separated and concentrated to give the title compound. Yield: 37%, $^1$H-NMR ($D_2O$): δ 7.57 (d, 1H, J=2.0); 7.47 (d, 1H, J=8.8 Hz); 7.33 (dd, 1H, J=7.0, 2.4 Hz); 4.13 (q, 1H, J=6.8 Hz); 1.39 (d, 6H, J=6.3 Hz).

Example 8

N-(2-Amino-benzothiazol-6-yl)-2-methylcarboximidamide

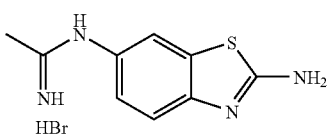

A mixture of benzothiazole-2,6-diamine (Example 1, 100 mg, 0.61 mmol) and thioacetimidic acid naphthalene-2-yl methyl ester hydrobromide (179 mg, 0.61 mmol) in 8 mL of anhydrous ethanol was stirred at room temperature for 16 hours. The reaction mixture was concentrated and partitioned between 5 mL of $H_2O$ and 20 mL of $Et_2O$. The aqueous layer was separated and washed with 20 mL of $Et_2O$. The aqueous layer was concentrated to give the title compound as a white solid. Yield: 80%, $^1$H-NMR($D_2O$): δ 7.61 (br s, 1H); 7.48 (d, 1H, J=8.3 Hz); 7.23 (d, 1H, J=6.8 Hz); 2.43 (s, 3H).

Example 9

N-(2-Amino-benzothiazol-6-yl)-2-thiophenecarboximidamide

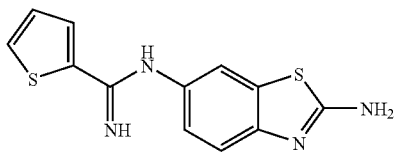

A mixture of benzothiazole-2,6-diamine (Example 1, 50 mg, 0.3 mmol) and thiophene-2-carboximidothioic acid phenyl ester hydrobromide (91 mg, 0.3 mmol) was stirred at room temperature for 17 hours. After this time a precipitate formed. The mixture was diluted with 4 mL of $Et_2O$ and filtered to give the title compound. Yield: 94%, $^1$H-NMR (DMSO-$d_6$): δ 11.30 (br s, 1H); 9.71 (s, 1H); 8.80 (s, 1H); 8.18 (m, 2H); 7.74 (m, 3H); 7.29 (m, 3H).

Example 10

N-(2,3-dihydro-N-ethyl-2-Imino-benzothiazol-6-yl)-2-ethylthiocarboximidamide

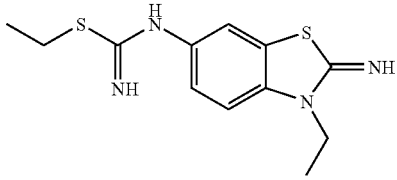

A suspension of 1-(2-amino-benzothiazol-6-yl)thiourea (Example 3, 30 mg, 0.187 mmol), ethyl iodide (15 μL, 0.18 mmol) and $K_2CO_3$ in 1 mL of DMF was heated at 85° C. in a sealed tube for 24 hours. About 20 equivalents of ethyl iodide was added over the period of 24 hours. The reaction mixture was diluted with $H_2O$ and extracted with 2×20 mL of $CH_2Cl_2$. The organic layer was dried over $Na_2SO_4$ and evaporated to give a yellow reside which was subjected to silica gel column chromatography (7.5% MeOH:92.5% $CH_2Cl_2$). Yield: 57.2%, $^1$H-NMR (DMSO-$d_6$): δ 8.69 (s, 1H); 8.08 (d, 1H, J=2.4 Hz); 7.93 (d, 1H, J=9.0 Hz); 7.44 (dd, 1H, J=7.0, 2.4 Hz); 4.47 (q, 2H, J=7.1 Hz); 3.77 (q, 2H, J=7.3 Hz); 1.31 (m, 6H).

Example 11

6-Nitro-2-(2-pyrrolidin-1-yl-ethylamino)benzothiazole

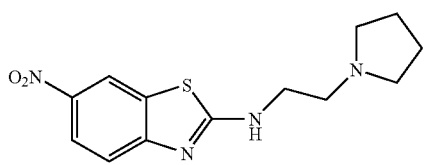

A mixture of 2-chloro-6-nitrobenzothiazole (250 mg, 1.16 mmol) and 2-pyrrolidin-1-yl-ethylamine (0.59 mL, 4.66 mmol) was heated at 100° C. for 4 hours then at 60° C. for 16 hours. After this time, the reaction mixture was filtered and the precipitate was washed with 2×5 mL of H₂O. The solid was subjected to silica gel column chromatography (7.5% MeOH:92.5% CH₂Cl₂) to give the title compound as a yellow residue. Yield: 20.6%, ¹H-NMR (DMSO-d₆): δ 8.80 (br s, 1H); 8.70 (d, 1H, J=2.4 Hz); 8.11 (dd, 1H, J=6.8, 2.4 Hz); 7.47 (d, 1H, J=8.8 Hz); 3.58 (m, 2H); 2.60 (m, 6H); 1.73 (m, 2H).

Example 12

6-Amino-2-(2-pyrrolidin-1-yl-ethylamino)benzothiazole

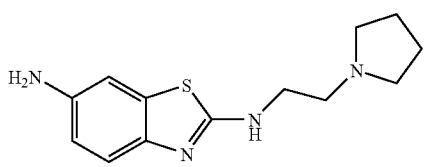

A suspension of 6-nitro-2-(2-pyrrolidin-1-ylethylamino) benzothiazole (Example 11, 50 mg, 0.17 mmol) and SnCl₂ (161 mg, 0.85 mmol) in 20 mL of ethanol (denatured) was heated at reflux for 4 hours. After cooling the mixture was partitioned between 50 mL of ethyl acetate and 20 mL of 1.0N aqueous NaOH. The organic layer was dried over sodium sulfate and concentrated to give a yellow residue which was subjected to silica gel column chromatography (5% 2M NH₃/MeOH:95% CH₂Cl₂). Yield: 65%, ¹H-NMR (CD₃OD): δ 8.70 (d, 1H, J=8.3 Hz); 8.47 (d, 1H, J=2.0 Hz); 8.21 (dd, 1H, J=6.3, 1.9 Hz); 5.05 (t, 2H, J=6.3 Hz); 4.28 (t, 2H, J=6.8 Hz); 4.14 (m, 4H); 3.33 (m, 4H).

Example 13

N-[2-(2-pyrrolidin-1-ylethylamino)-benzothiazol-6-yl]-2-thiophenecarboximidamide

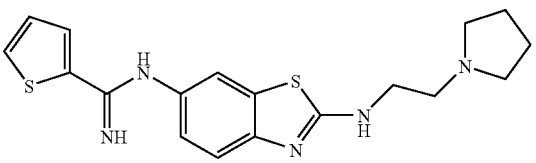

6-Amino-2-(2-pyrrolidin-1-yl-ethylamino)benzothiazole (Example 12, 28 mg, 0.11 mmol) and thiophene-2-carboximidothioic acid phenyl ester hydrobromide (32 mg, 0.11 mmol) in 3 mL of ethanol (denatured) was stirred at room temperature for 20 hours. The solvent was removed and the residue was partitioned between 5 mL of H2O and 10 mL of Et₂O. The aqueous layer was concentrated to give the title compound. ¹H-NMR (CD₃OD): δ 8.08 (m, 2H); 7.72 (d, 1H, J=2.0 Hz); 7.64 (d, 1H, J=8.0 Hz); 7.30 (m, 2H); 3.86 (t, 2H, J=5.9 Hz); 3.50 (m, 6H); 2.10 (m, 4H).

Example 14

1-Benzoyl-3-(2-fluoro-5-nitro-phenyl)-thiourea

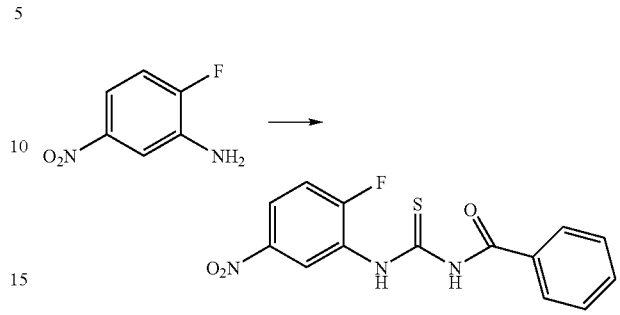

To 10 mL of THF was added 4-fluoro-3-nitroaniline (0.5 g, 3.2 mmol) along with benzoyl isothiocyanate (0.43 mL, 3.2 mmol). The resulting solution was stirred at rt for 17 hours after which, hexanes was added to the reaction mixture. The resulting precipitate was collected by filtration to give a beige solid (0.752 g, 74%). ¹H-NMR (DMSO d6) δ: 12.8 (br s, 1H), 12.0 (br s, 1H), 9.18 (d, 1H, J=3.9), 8.25 (m, 1H), 8.01 (d, 2H, J=7.7 Hz), 7.71–7.66 (m, 2H), 7.58–7.54 (m, 2H); MS (ESI) 320.2 (M+1, 45%), 299.8 (100%).

Example 15

5-Nitro-benzothiazol-2-ylamine

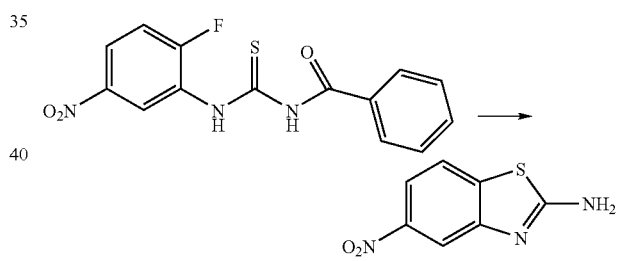

To a solution of methanol (1.6 L) was added sodium methoxide (8.64 g). While stirring, 1-benzoyl-3-(2-fluoro-5-nitro-phenyl)-thiourea (16 g) was added as a solid and the mixture stirred at room temperature for 17 hours. After this time, the reaction mixture was cooled in an ice bath and then filtered. The precipitate was washed with water (7.10 g, 86%). ¹H-NMR δ: 8.05 (d, 1H, J=2.2 Hz), 7.97 (brs, 2H), 7.93 (s, 1H), 7.90 (d, 1H, J=2.2 Hz); MS (ESI) 195.8 (M+1, 100%).

Example 16

5-amino-benzothiazol-2-ylamine

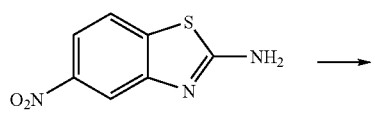

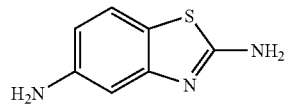

To a solution of ethanol (36 mL) was added 5-nitrobenzothiazol-2-ylamine (Example 15, 78 mg, 0.35 mmol) and tin dichloride dihydrate (449 mg, 2 mmol). The resulting mixture was heated at 80° C. for 4 hours. The solution was cooled to room temperature and the solvent was removed. The residue was dissolved in ethyl acetate and poured onto 50 mL of 1.5 N NaOH solution and extracted using ethyl acetate (3×30 mL). The combined organic layers were dried over MgSO4, filtered and concentrated to give a solid (43 mg, 66%). $^1$H NMR (DMSO d) δ: 7.23–7.19 (m, 3H), 6.59 (d, 1H, J=1.96 Hz), 6.32 (dd, 1H, J=2.18, 8.28 Hz), 4.88 (br s, 2H); MS (ESI) 166 (M+1, 100%).

Example 17

1-(2-Amino-benzothiazol-5-yl)-3-benzoyl-thiourea

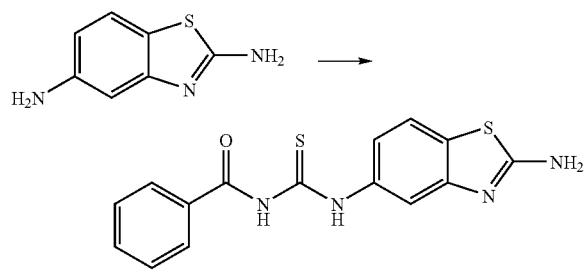

To a solution of anhydrous THF (6.7 mL) was added 5-amino-benzothiazol-2-ylamine (Example 16, 100 mg, 0.61 mmol) and benzoyl isothiocyanate (0.08 mL, 1 equiv). The resulting mixture was stirred at room temperature for 2 hours, after which the solvent was evaporated and the residue was washed with a 1:1 mixture of ether/hexanes (0.164 g, 83%). $^1$H NMR (DMSO d6) δ: 12.61 (s, 1H), 11.53 (s, 1H), 7.99 (d, 1H, J=3.9 Hz), 7.76 (s, 1H), 7.69–7.65 (m, 2H), 7.59–7.53 (m, 4H), 7.25–7.23 (d, 1H, J=3.9 Hz); MS (ESI) 328.8 (M+1, 100%).

Example 18

(2-Amino-benzothiazol-5-yl)-thiourea

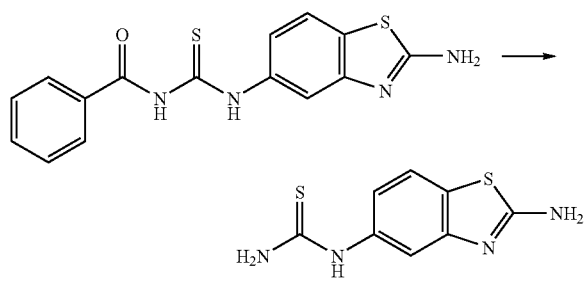

To a solution of anhydrous methanol (213 mL) was added sodium methoxide (1.15 g) and 1-(2-amino-benzothiazol-5-yl)-3-benzoyl-thiourea (Example 17, 3.5 g). The resulting mixture was stirred at room temperature for 3 hours. The mixture was concentrated and the residue was poured into water (300 mL). The mixture was extracted using ethyl acetate (3×200 mL). The combined organic fractions were dried over magnesium sulfate, filtered and concentrated (1.61 g, 67%). $^1$H-NMR (DMSO d6) δ: 9.64 (s, 1H), 760–7.37 (m, 6H), 6.96 (d, 1H, J=8.3 Hz); MS (ESI) 224.8 (M+1, 100%).

Example 19

1-(2-Amino-benzothiazol-5-yl)-3-ethyl-thiourea

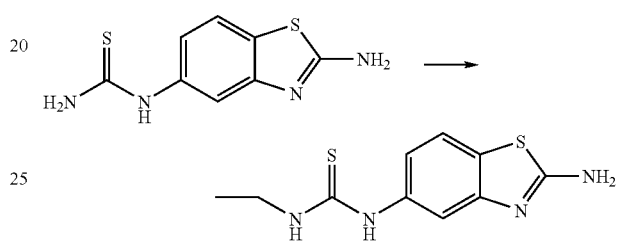

To a solution of the urea of Example 19 (50 mg) in anhydrous DMF (2.5 mL) was added ethyl iodide (18 µL) and K$_2$CO$_3$ (138 mg). The resulting mixture was stirred at room temperature for 22 hours. The mixture was poured into water (25 mL) and extracted using dichloromethane (3×25 mL). The combined organic layers were dried over magnesium sulfate, filtered and concentrated. The residue was chromatographed on silica gel using a solution of 10% methanol and 90% dichloromethane (18.8 mg, 45%). $^1$H —NMR (CDCl$_3$) δ: 7.48 (d, 1H, J=8.3), 6.97 (d, 1H, J=1.9 Hz), 6.67 (dd, 1H, J=8.3, 1.9 Hz), 2.97 (q, 2H, J=7.3 Hz), 1.33 (t, 3H, J=7.3); MS (ESI) 252.8 (M+1, 100%).

Example 20

N-(2-Amino-benzothiazol-5-yl)-thiophene-2-carboxamidine hydrobromide

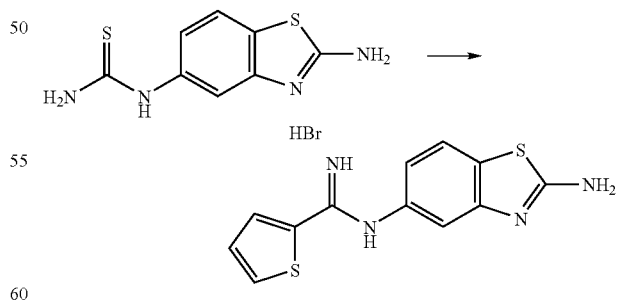

To a solution of the amino urea compound (Example 18, 35 mg, 0.21 mmol) in ethanol (1.4 mL) was added thiophene-2-carboximidothioic acid phenyl ester hydrobromide (63.7 mg, 0.21 mmol). The mixture was stirred at room temperature for 17 hours and then diluted with diethyl ether. The light yellow precipitate was collected by filtration (64.8 mg, 93%). ¹H-NMR (DMSO d6) δ: 11.36 (br s, 1H), 9.72 (br s, 1H), 8.83 (br s, 1H), 8.17 (d, 1H, J=4.68 Hz).

Example 21

N5-Thiazol-2-yl-benzothiazole-2,5-diamine

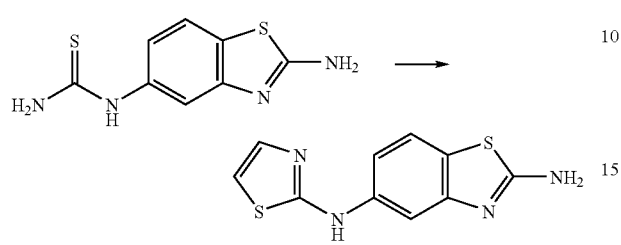

To a solution of ethanol (12 mL) was added the urea compound (Example 18, 50 mg, 0.22 mmol) along with chloroacetyaldehyde (0.12 mL, 0.94 mmol). The resulting mixture was heated at reflux for 24 hours. The mixture was then cooled to room temperature and the solvent was evaporated. Water (25 mL) was added to the residue and the pH was adjusted to 9 using sodium carbonate solution. The mixture was extracted using ethyl acetate (3×15 mL). The combined organic layers were dried over MgSO₄, filtered and concentrated (18.8 mg, 33%).%). ¹H-NMR (CDCl₃) δ: 7.66 (d, 1H, J=2.2 Hz), 7.47 (d, 1H, J=8.54), 7.21–7.18 (m, 2H), 6.73 (d, 1H, J=3.9 Hz); MS (ESI) 248.8 (M+1, 100%).

Example 22(a)

[2-(4-Bromo-phenyl)-ethyl]-(6-nitro-benzothiazol-2-yl)-amine

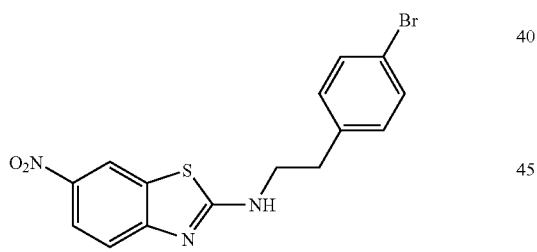

2-Chloro-6-nitro-benzothiazol (200 mg, 0.93 mmol) was placed in a 15 mL vial equipped with a stirring bar and septum. The vial was purged with argon and charged with DMF (1.0 mL). Diisopropyl-ethylamine (0.37 mL, 2 eq.) was added resulting in a reddish solution. 2-(4-Bromo-phenyl)-ethylamine (186 mg, 1 eq.) in DMF (1.0 mL) was added via syringe. The dark solution was then heated to 110° C. for 30 minutes in an aluminum block. The mixture was cooled in an ice bath and diluted with water (10 mL) while stirring vigorously. A dark precipitate formed. An additional 5 mL of water was added after stirring for 10 minutes and the product then collected by vacuum filtration. The product was washed with distilled water (2×10 mL) and dried under suction. The sample was dried under high vacuum (0.8 torr, 110° C., 20 hours) to give a solid (198 mg, 61%). ¹H NMR (CDCl₃) δ: 8.5 (s, 1H), 8.21 (br d, 1H, J=7.7 Hz), 7.48 m (3H), 7.10 (d, 2H, J=7.7 Hz), 5.68 (br s, 1H), 3.75 (br t, 3H), 2.99 (br t, 3H).

In a like manner, the following additional compounds were prepared:

(b) (6-Nitro-benzothiazol-2-yl)-(tetrahydro-pyran-4-yl)-amine

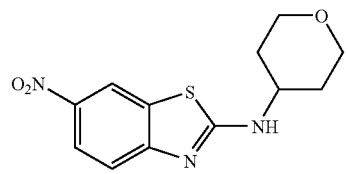

Yield: Yellow solid (179 mg, 69%). ¹H NMR (CDCl₃) δ: 7.38 (d, 1H, J=8.9 Hz), 6.96 (d, 1H, J=2.4 Hz), 6.70 (dd, 1H, J=8.9, 2.4 Hz), 3.83 (m, 5H), 3.55 (m, 4H), 2.93 (m, 1H).

(c) (6-Nitro-benzothiazol-2-yl)-(2-pyridin-2-yl-ethyl)-amine

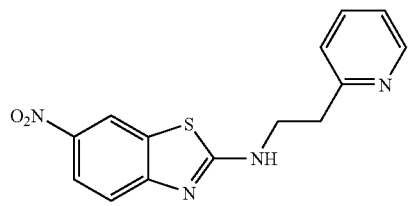

Yield: Yellow solid (145 mg, 52%). ¹H NMR (CDCl₃) δ: 8.6–8.49 (m, 2H), 8.22–8.18 (m, 1H), 7.64 (m, 1H), 7.50 (d, 1H, J=8.9 Hz), 7.22 (m, 3H), 3.91 (br t, 2H), 3.20 (t, 2H, J=5.6 Hz).

Example 23(a)

4-(6-Nitro-benzothiazol-2-ylamino)-butan-1-ol

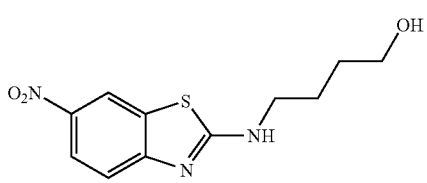

In an oven fried vial charged with 4-amino-1-butanol (172 μl, 2 eq.), 2-chloro-6-nitro-benzothiazol (200 mg, 0.93 mmol) and diisopropyl-ethylamine (1 mL) was added DMF (5 mL). The dark brown mixture was heated at 100° C. for 2 hours. After cooling, the mixture was diluted with 20 mL of water and extracted with ethyl-acetate (50 mL). The ethyl acetate layer was washed with brine, dried over MgSO₄ and then evaporated to give a dark residue. This residue was subjected to silica gel chromatography (7% 2M ammonia/methanol in CH₂Cl₂) to give the desired product (45 mg, 18%). ¹H NMR (CD₃OD) δ: 8.55 (d, 1H, J=2.3 Hz), 8.17 (dd, 1H, J=2.3, 8.9 Hz), 7.47 (d, 1H, J=8.9 Hz), 3.63 (m, 3H), 3.53 (t, 2H, J=6.8 Hz), 1.80–1.75 (m, 2H), 1.70–1.65 (m, 2H); MS (M+1, 268).

In a like manner the following additional compounds were prepared:

(b) [2-(3H-Imidazol-4-yl)-ethyl]-(6-nitro-benzothiazol-2-yl)-amine

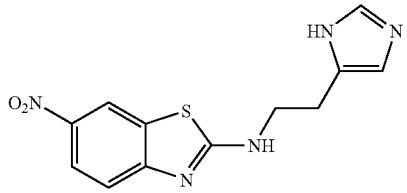

Yield: 80 mg (30%) of a solid. $^1$H NMR (CD$_3$OD) δ: 8.50 (d, 1H, J=2.5 Hz), 8.14 (dd, 1H, J=2.5, 8.9 Hz), 7.64 (s, 1H), 7.44 (d, 1H, J=8.9 Hz), 6.92 (s, 1H), 3.75 (t, 2H, J=7.0 Hz), 2.98 (t, 2H, J=7.0 Hz); MS (M+1, 290).

(c) (3-Imidazol-1-yl-propyl)-(6-nitro-benzothiazol-2-yl)-amine

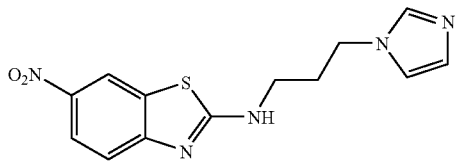

Yield: 70 mg (25%). $^1$H NMR (CD$_3$OD) δ: 8.52 (d, 1H, J=2.0 Hz), 8.15 (dd, 1H, J=2.0, 8.9 Hz), 7.71 (s, 1H), 4.18 (t, 2H, J=6.9 Hz), 3.50 (t, 2H, J=6.9 Hz), 2.20 (m, 2H); MS (M+1, 304).

(d) [2-(3-Chloro-phenyl)-ethyl]-(6-nitro-benzothiazol-2-yl)-amine

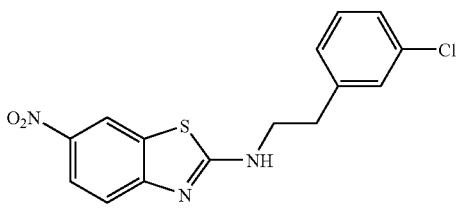

Yield: 433 mg (70%).

Example 24

(1-Benzyl-piperidin-4-yl)-(6-nitro-benzothiazol-2-yl)-amine

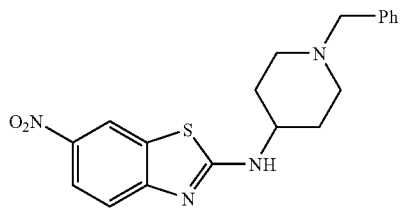

2-Chloro-6-nitro-benzothiazol (200 mg, 0.93 mmol) was placed in a 15 mL vial equipped with a stribar and septum. The vial was purged with argon and charged with DMF (1.0 mL). Diisopropyl-ethylamine (0.37 mL, 2 eq.) was added resulting in a reddish solution. Amino-4-benzylpiperidine (177 mg, 1 eq.) in DMF (1.0 mL) was added via syringe. The dark solution was then heated to 110° C. for 30 minutes in an aluminum block. The mixture was cooled in an ice bath and diluted with water (10 mL) while stirring vigorously. The compound oiled out. Ethyl acetate (25 mL) was added followed by 2 M NaOH (5 mL) was added and the layers shaken and separated. The aqueous phase was extracted with ethyl acetate (25 mL). The combined organic fractions were washed with brine (2×24 mL), dried over MgSO$_4$, filtered and evaporated to give a brown oil. The oil was purified by chromatography on silica gel (2% 2M ammonia/methanol in CH$_2$Cl$_2$) to give a yellow foam (166 mg, 47%). $^1$H NMR (CDCl$_3$) δ: 8.50 (d, 1H, J=2.4 Hz), 8.20 (dd, 1H, J=2.4, 8.9 Hz), 7.51 (d, 1H, J=8.9 Hz), 7.32 (m, 5H), 5.63 (d, 1H, J=6 Hz), 3.70 (br s, 1H), 3.55 (s, 2H), 2.89 (m, 2H), 2.28–2.11 (m, 4), 1.73–1.56 (m, 2H).

Example 25(a)

[2-(1-Methyl-pyrrolidin-2-yl)-ethyl]-(5-nitro-benzothiazol-2-yl)-amine

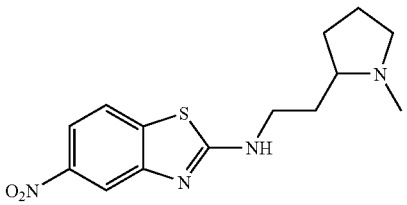

To a pressure bottle charged with 2-amino-5-nitro-benzothiazole (Example 15, 0.50 g, 2.56 mmol), 2-(2-chloroethyl)-1-methyl-pyrrolidine hydrochloride (0.57 g, 1.2 eq.) and K$_2$CO$_3$ (1.06 g, 3 eq.) was added dry DMF (5 mL). The mixture was heated at 130° C. for 24 hours. After cooling to room temperature, the reaction mixture was poured into water (100 mL) and extracted with ethyl acetate (3×100 mL). The combined organic fractions were dried over MgSO$_4$, filtered and concentrated. The residue was chromatographed on silica gel (10% ammonia/methanol in CH$_2$Cl$_2$) (177 mg, 23%). $^1$H NMR (CDCl$_3$) δ: 8.25 (d, 1H, J=1.8 Hz), 7.87 (dd, 1H, J=1.8, 8.7 Hz), 7.59 (d, 1H, J=8.7

Hz), 3.54 (m, 2H), 3.43 (m, 2H), 2.40 (m, 1H), 2.33 (s, 4H), 2.17 (dd, 1H, J=8.9, 17.7), 1.93–1.66 (m, 6H).

In a like manner, the following additional compound was prepared:

(b) N,N-Dimethyl-N'-(5-nitro-1H-inden-2-yl)-ethane-1,2-diamine

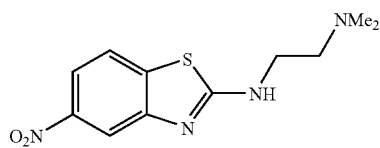

In a similar manner from 2-amino-5-nitro-benzothiazole (Example 15) and 2-chloroethylamine hydrochloride, the title compound was obtained after chromatography on silica (215 mg, 32%). $^1$H NMR (CD$_3$OD) δ: 8.17 (d, 1H, J=1.65 Hz), 7.91 (dd, 1H, J=1.7, 8.4 Hz), 7.76 (d, 1H, J=8.4 Hz), 3.64 (t, 2H, J=6.7 Hz), 2.70 (t, 2H, J=6.7), 2.37 (s, 6H).

Example 26

(2-Morpholin-4-yl-ethyl)-(6-nitro-benzothiazol-2-yl)-amine

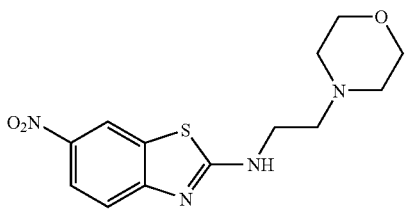

To a mixture of 2-chloro-6-nitrobenzothiazole (1.00 g, 4.66 mmol) in water (9.0 mL) was added 2-morpholin-4-yl-ethylamine (2.45 mL, 18.6 mmol). The dark reaction mixture was stirred under argon and refluxed for 4.5 hours at which time the reaction became red-brown in colour. The mixture was then cooled to 65° C. and stirred an additional 17.75 hours. The precipitate was then collected by suction filtration after cooling to room temperature giving a yellow solid (377 mg, 26%). $^1$H NMR (DMSO-d$_6$) δ: 8.69 (d, 1H, J=2.1 Hz), 8.10 (dd, 1H, J=2.1, 8.9 Hz), 7.46 (d, 1H, J=8.9 Hz), 3.59 (m, 6H), 2.55 (t, 2H, J=6.2 Hz), 2.51 (m, 4H), 2.43 (m, 4H).

Example 27(a)

N2-(2-Pyridin-2-yl-ethyl)-benzothiazole-2,6-diamine

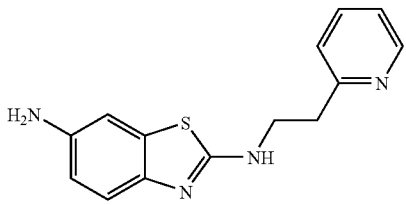

(6-Nitro-benzothiazol-2-yl)-(2-pyridin-2-yl-ethyl)-amine (Example 22(c), 46.6 mg, 0.155 mmol) and tin(II) chloride dihydrate (175 mg, 5 eq) and ethanol (reagent grade, 5 mL) were heated in a sealed vial at 88–90° C. for 4 hours. The solution was diluted with 3N NaOH (3 mL) and ethyl acetate (5 mL). The layers were separated and the aqueous layer extracted with ethyl acetate (2×5 mL). The combined ethyl acetate extracts were dried over MgSO$_4$, filtered and evaporated. The solid was subjected to chromatography on silica gel (5% 2M ammonia/methanol in CH$_2$Cl$_2$) giving green foam. Yield (37.3 mg, 89%). $^1$H NMR (CDCl$_3$) δ: 8.53 (m, 1H), 7.58 (dd, 1H, J=7.7, 9.6 Hz), 7.35–7.26 (m, 2H), 7.18–7.10 (m, 2H), 6.90 (d, 1H, J=2.4), 6.65 (dd, 1H, J=2.4, 8.9 Hz), 6.16 (br s, 1H), 3.81 (t, 2H, J=6.1 Hz), 3.2 (br s, NH$_2$), 3.13 (t, 2H, J=6.1).

In a like manner, the following additional compound was prepared:

(b) N2-(1-Benzyl-piperidin-4-yl)-benzothiazole-2,6-diamine

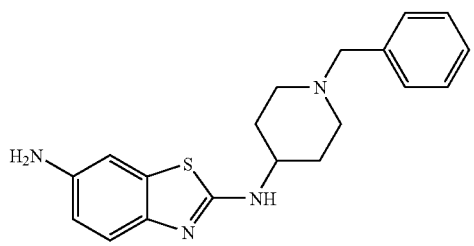

In a like manner from (1-benzyl-piperidin-4-yl)-(6-nitro-benzothiazol-2-yl)-amine (Example 24), a yellow oil was obtained after purification by chromatography (5% 2M ammonia/methanol in CH$_2$Cl$_2$ (42.3 mg, 81%). $^1$H NMR (CDCl$_3$) δ: 7.4–7.2 (m, 6H), 6.91 (d, 1H, J=2.0 Hz), 6.66 (dd, 1H, J=2.0, 8.5 Hz), 5.20 (br s, 1H), 3.59 (br s, 2H), 3.51 (s, 2H), 2.85–2.70 (m, 2H), 2.25–2.05 (m, 4H), 1.7–1.5 (m, 2 H).

Example 28

N2-[2-(1-Methyl-pyrrolidin-2-yl)-ethyl]-benzothiazole-2,5-diamine

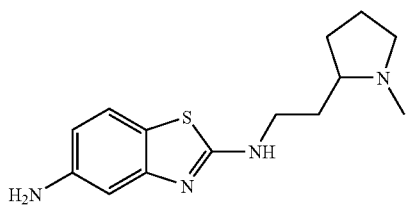

To 5 mL of ethanol was added [2-(1-Methyl-pyrrolidin-2-yl)-ethyl]-(5-nitro-benzothiazol-2-yl)-amine (Example 25(a), 177.4 mg, 0.577 mmol) and tin(II) chloride dihyrdate (948 mg, 5 eq.). The resulting solution was heated at reflux for 4 hours. After cooling to room temperature, the mixture was poured onto 100 mL of a 1.5 M NaOH solution. The mixture was extracted using ethyl acetate (3×100 mL). The combined organic fractions were dried over MgSO$_4$, filtered and concentrated. The residue was chromatographed on silica gel using 10% 2M ammonia/methanol in dichloromethane (98.4 mg, 62%). $^1$H NMR (CDCl$_3$) δ: 7.32 (d, 1H, J=8.5 Hz), 6.91 (d, 1H, J=1.9 Hz), 6.49 (dd, 1H, J=1.9, 8.5 Hz), 3.67 (br s, NH$_2$), 3.51 (m, 2H), 3.13–3.09 (m, 1H), 2.36 (s, 4H), 2.19 (m, 1H), 1.93–1.68 (m, 6H).

Example 29

N2-(2-Dimethylamino-ethyl)-benzothiazole-2,5-diamine

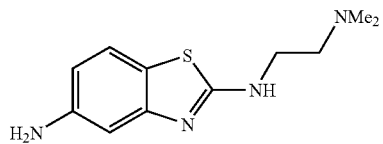

To a solution of N,N-dimethyl-N'-(5-nitro-1H-inden-2-yl)-ethane-1,2-diamine (Example 25(b), 200 mg, 0.75 mmol) dissolved in ethanol (6.7 mL) was added tin(II) chloride dihydrate (1.23 g, 5 eq.). The resulting mixture was refluxed for 4.5 hours. After cooling to room temperature, the solvent was evaporated. The residue was partitioned between 1.5 N NaOH (100 mL) and ethyl acetate (100 mL). The aqueous phase was extracted with ethyl acetate (2×100 mL). The combined organic fractions were dried over MgSO$_4$, filtered and concentrated. The residue was chromatographed on a silica gel column (10% 2M ammonia/methanol in CH$_2$Cl$_2$) to give the aniline (98.2 mg, 56%).

Example 30

4-(6-Amino-benzothiazol-2-ylamino)-butan-1-ol

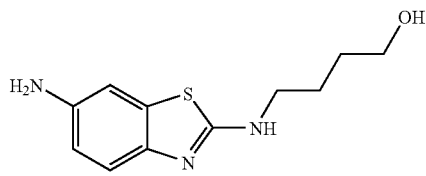

To a solution of the nitro compound (Example 23(a). 83 mg, 0.31 mmol) in ethanol (6 mL) was added tin(II) chloride dihydrate (350 mg, 1.55 mmol). The reaction mixture was heated at reflux under argon for 2.5 hours. The solution was cooled to room temperature and diluted with ethyl acetate (50 mL). The organic layer was extracted with 3N NaOH (3×30 mL). The organic extracts were dried over MgSO$_4$, filtered and concentrated. The resulting oil was purified by silica gel chromatography (5% 2M ammonia/methanol in CH$_2$Cl$_2$) to afford a dark yellow solid (72 mg, 98%). $^1$H NMR (CD$_3$OD) δ: 7.22 (d, 1H, J=), 7.01 (s, 1H), 6.74 (d, 1H, J=6.9 Hz), 3.61 (s, 2H), 3.41 (s, 2H), 3.33 (s, 1H, OH), 1.73 (b s, 2H), 1.66 (b s, 2H).

Example 31

N2-(3-Imidazol-1-yl-propyl)-benzothiazole-2,6-diamine

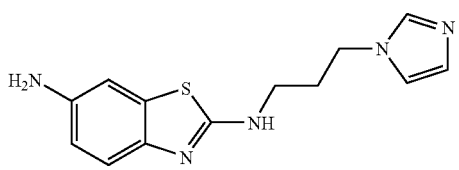

To a solution of the nitro compound (Example 23(c), 50 mg, 0.16 mmol) in ethanol (3 mL) and THF (2 mL) was added tin(II)chloride dihydrate (190 mg, 0.84 mmol). The solution was heated to reflux under argon for 3.5 hours. The solution was cooled to room temperature and diluted with ethyl acetate (50 mL). The solution was extracted with 3N NaOH (3×30 mL). The organic layer was dried over MgSO$_4$, filtered and concentrated. The resulting oil was purified by chromatography on silica (10% 2M ammonia/methanol in CH$_2$Cl$_2$) to give the desired product (32.4 mg, 74%).

Example 32

N2-[2-(3-Chloro-phenyl)-ethyl]-benzothiazole-2,6-diamine

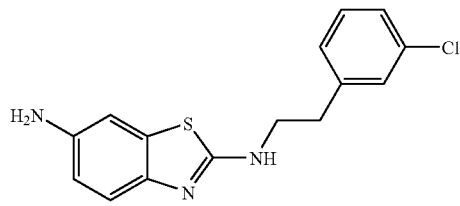

To a solution of the nitro compound (Example 23(d), 432 mg, 1.29 mmol) in ethanol (5 mL) and THF (3 mL) was added tin(II) chloride dihydrate (1.46 g, 6.47 mmol). The solution was stirred at reflux for 3.5 hours. The solution was cooled to room temperature and extracted with 3N NaOH (3×30 mL). The organic extracts were dried with MgSO$_4$, filtered and concentrated. The resulting oil was purified by silica gel chromatography (2.5% 2M ammonia/methanol in CH$_2$Cl$_2$) to afford a dark yellow solid (168 mg, 43%).

Example 33(a)

N2-[2-(4-Bromo-phenyl)-ethyl]-benzothiazole-2,6-diamine

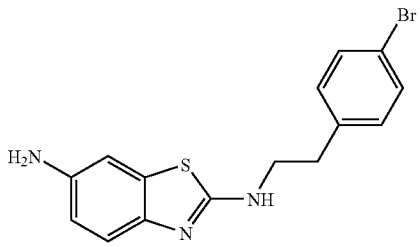

[2-(4-Bromo-phenyl)-ethyl]-(6-nitro-benzothiazol-2-yl)-amine (Example 22(a), 108.5 mg, 0.364 mmol) and tin(II) chloride dihydrate (411 mg, 5 eq.) were placed in a flask equipped with a septum and stirring bar. The flask was purged with argon and ethanol (reagent grade, 10 mL) was added. The yellow solution was then refluxed for 5 hours and the solvent evaporated. The thick yellow oil was dissolved in ethyl acetate (20 mL) and extracted with 3N sodium hydroxide solution (3×5 mL). The aqueous phase was extracted with ethyl acetate (10 mL) and the combined extracts dried over MgSO$_4$, filtered and concentrated. The reddish oil was purified by chromatography on silica gel (1:1 hexanes/:ethyl acetate). Yield: 71.2 mg. ¹H NMR (CDCl₃) δ: 7.43 (d, 2H, J=8.5), 7.35 (d, 1H, J=8.5), 7.08 (d, 2H, J=8.5 Hz), 6.92 (d, 1H, J=2.4 Hz), 6.87 (dd, 1H, J=2.4, 8.5), 5.35 (br s, 1H), 3.62 (t, 2H, J=6.9), 3.5 (br s, 2H), 2.92 (t, 2H, J=6.9).

In a like manner the following additional compound was prepared:

(b) N2-(Tetrahydro-pyran-4-yl)-benzothiazole-2,6-diamine

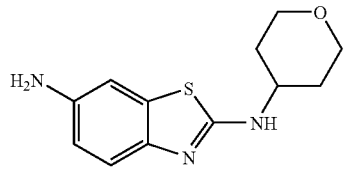

From Example 22(b). Yellow solid (34.1 mg, 64%). ¹H NMR (CDCl₃) δ: 7.36 (m, 1H), 6.95 (m, 1H), 6.7 (m, 1H), 5.1 (br s, 1H), 3.85 (m, 4H), 3.6 (br s, 2H), 2.93 (m, 4H).

Example 34

N2-[2-(3H-Imidazol-4-yl)-ethyl]-benzothiazole-2,6-diamine

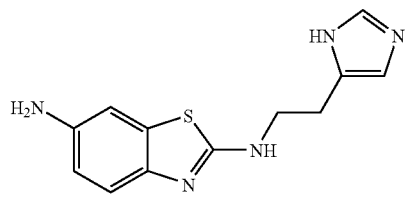

To a solution of [2-(3H-Imidazol-4-yl)-ethyl]-(6-nitro-benzothiazol-2-yl)-amine (Example 23(b), 80 mg, 0.28 mmol) in ethanol (5 mL) and THF (1.5 mL) was added tin(II) chloride dihydrate (312 mg, 5 eq.). The mixture was heated at reflux for 2 hours. The reaction mixture was cooled to room temperature, diluted with ethyl acetate (50 mL) then treated with 2 M aqueous NaOH (20 mL). The organic layer was separated, dried over MgSO₄ and concentrated to give a yellow residue. The residue was subjected to silica gel column chromatography (10–15% 2M ammonia/methanol in CH₂Cl₂) to give the final product (41 mg, 56%). ¹H NMR (CD₃OD) δ: 7.65 (s, 1H), 7.23 (d, 1H, 8.5 Hz), 6.98 (d, 1H, J=1.8 Hz), 6.91 (s, 1H), 6.72 (dd, 1H, J=1.8, 8.5 Hz), 3.64 (t, 2H, J=7.3 Hz), 2.95 (t, 2H, J=7.3 Hz).

Example 35

N2-(2-Morpholin-4-yl-ethyl)-benzothiazole-2,6-diamine

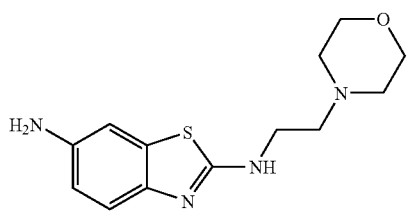

A mixture of (2-morpholin-4-yl-ethyl)-(6-nitro-benzothiazol-2-yl)-amine (Example 26, 250 mg, 0.81 mmol) and tin(II) chloride dihydrate (914 mg, 5 eq.) in ethanol (30 mL) was heated at reflux for 6 hours. The reaction mixture was concentrated, treated with 1.0 N NaOH solution (50 mL), and extracted with ethyl acetate (2×100 mL). The organic layer was dried over MgSO₄, concentrated and subjected to silica gel chromatography (10% 2M ammonia/methanol in CH₂Cl₂) to give the desired amine (175 mg, 77%). LCMS analysis (acetonitrile water, C18 silica) reveals 99.9% purity. MS (M+1, 279).

Example 36

Preparation of Amidines

Using the procedure described in Example 13, the following compounds were prepared:

(a) N-[2-(Tetrahydro-pyran-4-ylamino)-benzothiazol-6-yl]-thiophene-2-carboxamidine

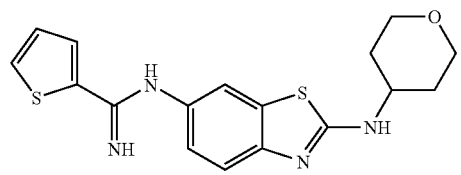

From Example 33(b). Yield: 22 mg of yellow oil. ¹H NMR (CDCl₃) δ: 7.55–7.38 (m 3H), 7.31–7.24 (m, 1H), 7.11–7.08 (m, 1H), 6.99–6.93 (m, 1H), 4.91 (br s, 1 H), 3.86–3.81 (m, 4H), 3.5 (t, 1H) 2.99–2.97 (m, 4H). MS (360, M+).

(b) N-{2-[2-(4-Bromo-phenyl)-ethylamino]-benzothiazol-6-yl}-thiophene-2-carboxamidine

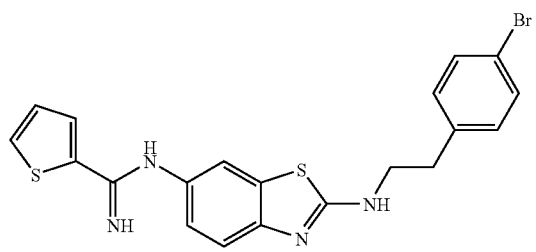

From Example 33(a). Yield: 30.4 mg of beige solid, 63% (HBr salt). An analytical sample was prepared by silica gel chromatography purification (2.5% 2M ammonia/methanol in dichloromethane) ¹H NMR (CDCl₃) δ: 7.55 (d, J=8.6), 7.48–7.43 (m, 4H), 7.48–7.43 (m, 3H), 7.28 (s, 2H), 7.15–7.10 (m, 3H), 7.0–6.97 (m, 1H), 5.32 (br s, 1H), 4.88 (br s, 2H), 3.71 (t, 2H, J=6.8), 2.99 (t, 2H, J=6.8). MS (M+1; 457, 459).

(c) N-[2-(2-Pyridin-2-yl-ethylamino)-benzothiazol-6-yl]-thiophene-2-carboxamidine

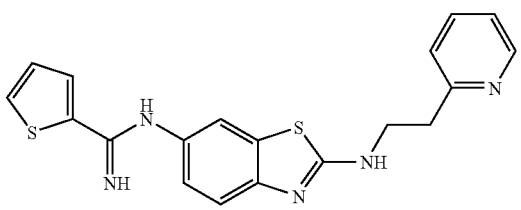

From Example 27(a). Yield: 42.5 mg of yellow solid, 67% (HBr salt). An analytical sample was obtained by purification using silica gel chromatography (5% 2M ammonia/methanol solution in dichloromethane) to give a yellow oil. $^1$H NMR (CDCl$_3$) δ: 8.57 (d, 1H, J=4.2), 7.63 (m, 1H), 7.51 (d, 1H, J=8.4), 7.45–7.42 (m, 2H), 7.23–7.19 (m, 3H), 7.10–7.09 (m, 1H), 6.96–6.94 (dd, 1H, J=1.65, 8.7 Hz), 6.28 (br s, 1H), 4.91 (br s, 2H), 3.88 (t, 2H, J=6.9 Hz), 3.18 (t, 2H, J=6.4 Hz). MS (M+1, 380).

(d) N-[2-(1-Benzyl-piperidin-4-ylamino)-benzothiazol-6-yl]-thiophene-2-carboxamidine

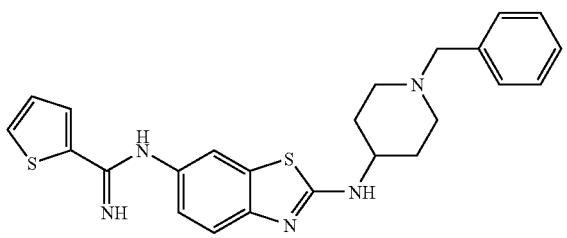

From Example 27(b). Yield: 52.4 mg, 0.09 mmol of a solid, 79% (HBr salt). The free base was prepared dissolving in methanol (1 mL) and diluting with ethyl acetate (10 mL) and washing with saturated sodium bicarbonate solution (5 mL). The aqueous phase was extracted with ethyl acetate and the combined organic layers dried over MgSO$_4$, filtered and concentrated to give a yellow oil (41.1 mg, 0.09 mmol). $^1$H NMR (CDCl$_3$) δ: 7.51 (d, 1H, J=8.5 Hz), 7.45–7.42 (m, 2H), 7.35–7.34 (m, 4H), 7.29–7.28 (m, 1H), 7.24 (d, J=1.8), 7.10 (m, 1H), 6.96 (dd, 1H, J=1.8, 8.5), 5.18 (br s, 1H), 4.85 (br s, 2H), 3.68 (bs, 1H), 3.56 (s, 2H), 2.87 (br d, 2H), 2.24 (t, 2H), 2.15 (br d, 2H), 1.67 (q, 2H). MS (M+1, 448).

(e) N-{2-[2-(3H-Imidazol-4-yl)-ethylamino]-benzothiazol-6-yl}-thiophene-2-carboxamidine

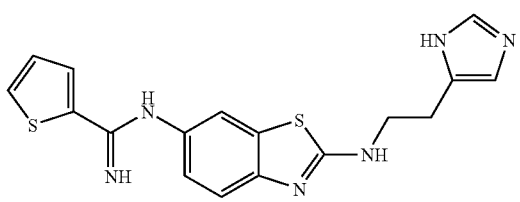

From Example 34. Yield: 27 mg (49%) of yellow solid. $^1$H NMR (CD$_3$OD) δ: 7.66 (d, 1H, J=3 Hz), 7.61 (s, 1H), 7.59 (d, 1H, J=4.8 Hz), 7.45 (d, 1H, 8.2), 7.25 (d, 1H, J=1.8 Hz), 7.14 (t, 1H, J=4.4 Hz), 6.95 (dd, 1H, J=1.8, 8.0 Hz), 6.90 (s, 1H), 3.69 (t, 2H, J=7 Hz), 3.37 (s, 2H), 3.33 (d, 1H, J=1.8 Hz), 2.97 (t, 2H, J=7 Hz). MS (M+1, 369).

(f) N-[2-(2-Morpholin-4-yl-ethylamino)-benzothiazol-6-yl]-thiophene-2-carboxamidine

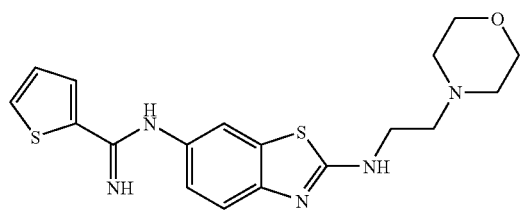

From Example 35. Yield: 115 mg (82%) of a yellow solid. $^1$H NMR (DMSO-d$^6$) δ: 7.74–7.70 (m, 2 H), 7.60 (d, 1H, J=4.9 Hz), 7.31 (d, 1H, J=8.5 Hz), 7.15 (s, 1H), 7.10 (t, J=4.4 Hz), 6.73 (d, 1H, J=7.4), 6.40 (br s, 2H), 3.61–3.58 (m, 4 H), 3.50–3.45 (m, 2H), 2.53 (m, 2H), 2.44 (m, 4H). MS (M+1, 388).

(g) N-[2-(2-Dimethylamino-ethylamino)-benzothiazol-5-yl]-thiophene-2-carboxamidine

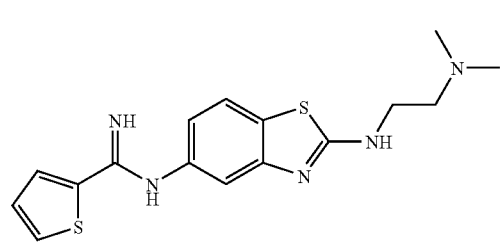

From Example 29. Yield: 76 mg (77%) of an oil. $^1$H NMR (CDCl$_3$) δ: 7.49 (d, 1H, J=8.2 Hz), 7.42 (m, 2H), 7.17 (s, 1H), 7.06 (t, 1H, J=4.2 Hz), 6.74 (dd, 1H, J=1.4, 8.1 Hz), 6.15 (br s, 1H), 4.95 (br s, 2H), 3.48 (t, 2H, J=5.73 Hz), 2.57 (t, 2H, J=5.7 Hz), 2.27 (s, 6H); MS (M+1, 346)

(h) N-{2-[2-(1-Methyl-pyrrolidin-2-yl)-ethylamino]-benzothiazol-5-yl}-thiophene-2-carboxamidine

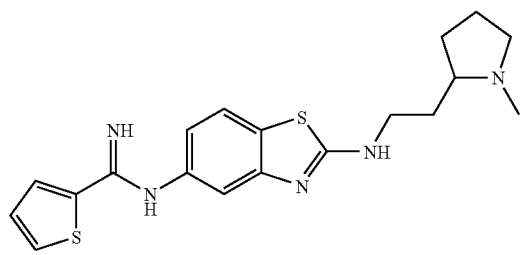

From Example 28. Yield: 123 mg (93%). $^1$H NMR (CDCl$_3$) δ: 7.47 (d, 1H, J=8.3 Hz), 7.42 (m, 2H), 7.21 (br s, 1H), 7.14 (d, 1H, J=1.7 Hz), 7.04 (m, 1H), 6.71 (d, 1H, J=7.4 Hz), 5.01 (br s, 2H), 3.46 (m, 2 H), 3.06 (m, 1H), 2.31 (s, 4H), 2.14 (dd, 1H), 1.9–1.6 (m, 6H); MS (M+1, 386)

(i) N {2-[2-(3-Chloro-phenyl)-ethylamino]-benzothiazol-6-yl}-thiophene-2-carboxamidine

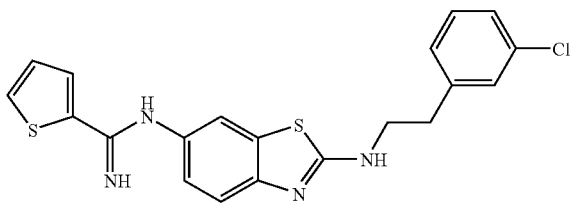

From Example 32. Yield: 130 mg (48%) of a shiny gold-colored solid. $^1$H NMR (CDCl$_3$) δ: 7.51 (d, 1H, J=8.3 Hz), 7.44 (m, 2H), 7.26 (m, 4H), 7-14–7.10 (m, 2H), 6.96 (dd, 1H, J=1.2, 7.9 Hz), 5.49 (b s, 1H), 4.92 (b s, 2H), 3.70 (t, 2H, J=6.9 Hz), 2.99 (t, 2H, J=6.9 Hz).

(j) N-[2-(4-Hydroxy-butylamino)-benzothiazol-6-yl]-thiophene-2-carboxamidine

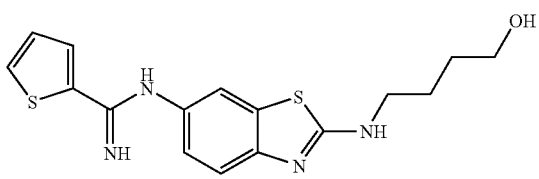

From Example 30. Yield: 44.9 mg of a dark yellow-brown oil (35%). $^1$H NMR (CDCl$_3$) δ: 7.53 (d, 1H, J=8.2 Hz), 7.45 (m, 2H), 7.24 (s, 1H), 7.12 (d, J=3.5 Hz), 6.97 (d, 1H, J=8.4 Hz), 3.76 (t, 2H), 3.51 (m, 3H), 1.83 (m, 2H), 1.74 (m, 2H).

(k) N-[2-(3-Imidazol-1-yl-propylamino)-benzothiazol-6-yl]-thiophene-2-carboxamidine

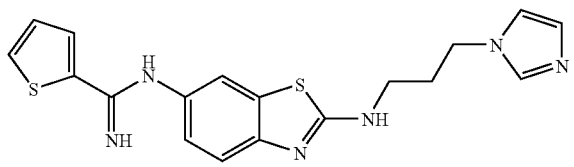

From Example 31. Yield: 38 mg of a thick yellow oil (78%). $^1$H NMR (CDCl$_3$) δ: 7.55 (m, 2H), 7.45 (m, 2H), 7.28 (m, 1H), 7.11 (s, 2H), 6.98 (s, 2H), 5.33 (b s, 1H), 4.90 (b s, 2H), 4.13 (m, 2H), 3.50 (m, 2H), 2.23 (m, 2H).

Example 37

1-Benzoyl-3-[2-(1-benzyl-piperidin-4-ylamino)-benzothiazol-6-yl]-thiourea

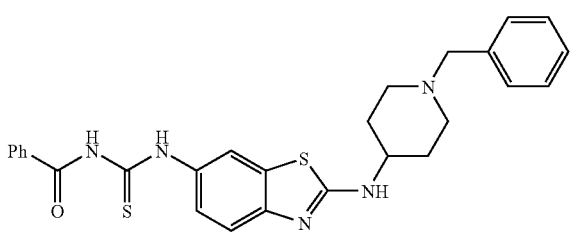

N2-(1-Benzyl-piperidin-4-yl)-benzothiazole-2,6-diamine (Example 27b, 39 mg, 0.12 mmol) was stirred with benzoylisothiocyanate (17 µl, 1.1 eq.) in dry THF at room temperature under argon for 24 hours. The solvent was evaporated to give a yellow oil. The oil was purified by chromatography on silica gel (30% ethyl acetate/hexanes) to give a yellow oil (60.7 mg, 100%).

Example 38

[2-(1-Benzyl-piperidin-4-ylamino)-benzothiazol-6-yl]-thiourea

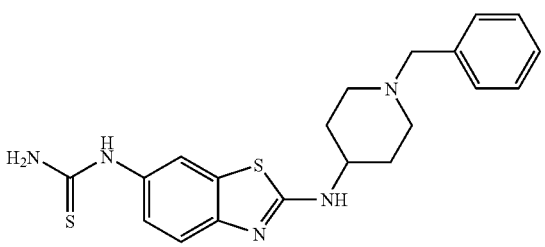

1-Benzoyl-3-[2-(1-benzyl-piperidin-4-ylamino)-benzothiazol-6-yl]-thiourea (Example 37, 29 mg, 0.058 mmol) was placed in an argon purged flask. THF (3 mL) was added followed by 2M NaOH (0.13 mL, 4.4 eq.). The mixture was heated to reflux for 44 hours. The solvent was evaporated. The mixture was diluted with water (2 mL) and ethyl acetate (10 mL). The layers were separated and the aqueous phase (saturated with NaCl) extracted with ethyl acetate (2×10 mL). The combined organic fractions were dried over MgSO$_4$, filtered and evaporated to give a yellow oil which was dried under high vacuum overnight. (crude yield: 25.2 mg). The product was used directly in the subsequent step (Example 39).

Example 39

N2-(1-Benzyl-piperidin-4-yl)-N-6-thiazol-2-yl-benzothiazole-2,6-diamine

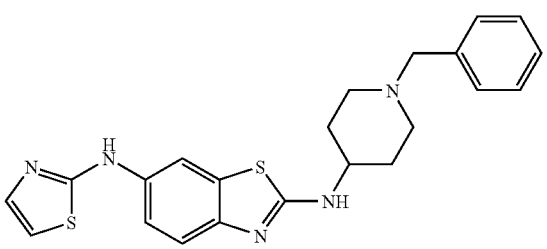

A mixture of N2-(1-Benzyl-piperidin-4-yl)-benzothiazole-2,6-diamine (Example 27(b), 25.2 mg, 0.063 mmol) and 50% aqueous chloroacetaldehyde (20 µL) were refluxed in ethanol for 5 hours. An additional 70 µL were added and refluxed continued for 24 hours and then at room temperature for 3 days. The solvent was removed and the product subjected to chromatography on silica gel (2.5–10% 2M ammonia/methanol in CH$_2$Cl$_2$) to give a yellow oil (10.3 mg, 39%). $^1$H NMR (CDCl$_3$) δ: 7.76 (d, 1H, J=2.1 Hz), 7.48 (d, 1H, J=8.6 Hz), 7.35 (m, 5H), 7.32–7.26 (m, 3H), 7.20 (dd, 1H, J=2.2, 8.4 Hz), 6.60 (d, 1H, J=3.6 Hz), 5.40 (br s, 1H), 3.67 (m, 1H), 3.57 (s, 2H), 2.9–2.87 (m, 2H) 2.25 (t, 2H), 2.17–2.13 (m, 2H), 1.71–1.62 (m, 2H). MS (M+1, 422).

Example 40

1-Benzoyl-3-{2-[2-(4-bromo-phenyl)-ethylamino]-benzothiazol-6-yl}-thiourea

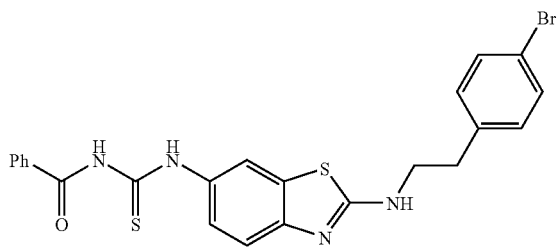

N2-[2-(4-Bromo-phenyl)-ethyl]-benzothiazole-2,6-diamine (Example 33(a), 71 mg, 0.205 mmol) was dissolved in tetrahydrofuran (3 mL). Benzoyl isothiocyanate (20 μl, 1.1 eq) was added and the mixture stirred at room temperature for 24 hours. The solvent was evaporated to give a yellow solid. The solid was dissolved in $CH_2Cl_2$ (5 mL) and absorbed onto silica gel. The absorbed compound was loaded onto a silica column and eluted with a mixture of ethyl acetate/hexanes (1:1) to give a yellow solid (99 mg, 95%). $^1$H NMR ($CDCl_3$) δ: 12.61 (s, 1H), 9.10 (s, 1H), 8.19 (s, 1H), 7.90 (d, 2H, J=8.5 Hz), 7.67–7.43 (m, 8H), 7.12 (d, 2H, J=8.5 Hz), 3.69 (t, 2H, J=6.9 Hz), 2.97 (d, 2H, J=6.9 Hz).

Example 41

{2-[2-(4-Bromo-phenyl)-ethylamino]-benzothiazol-6-yl}-thiourea

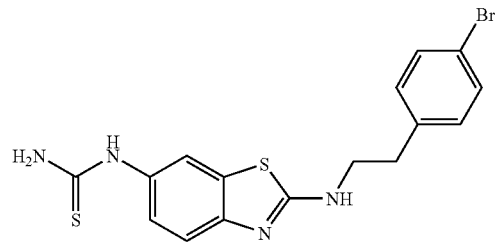

1-Benzoyl-3-{2-[2-(4-bromo-phenyl)-ethylamino]-benzothiazol-6-yl}-thiourea (Example 38, 71.1 mg, 0.139 mmol) was dissolved in tetrahydrofuran (3 mL). Aqueous NaOH (2M, 0.3 mL) was added and the mixture refluxed under argon for 44 hours. The mixture was cooled to room temperature and the solvent evaporated. Water (2 mL) and ethyl acetate (10 mL) were added and the layers separated. The aqueous phase was saturated with NaCl before extraction. An additional 10 mL of ethyl acetate was added and the layers separated. The combined extracts were dried over $MgSO_4$, filtered and evaporated to give a yellow solid (51.3 mg, 91%).

Example 42

1 {2-[2-(4-Bromo-phenyl)-ethylamino]-benzothiazol-6-yl}-2-ethyl-isothiourea

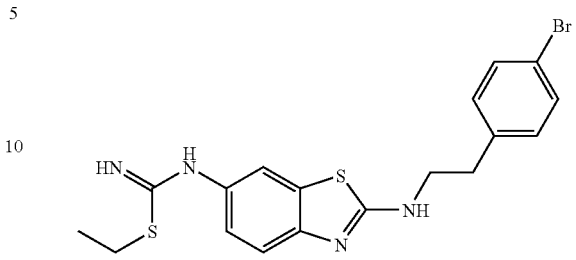

{2-[2-(4-Bromo-phenyl)-ethylamino]-benzothiazol-6-yl}-thiourea (Example 39, 51.3 mg, 0.126 mmol) was dissolved in dry DMF (0.5 mL). Ethyl iodide (11 μl, 1.1 eq) was added and the yellow solution stirred at room temperature for 23 hours. The solution was diluted with ethyl acetate (10 mL) and extracted with ice water (2 mL) followed by ice cold brine (3×2 mL). The product was dried over $MgSO_4$, filtered and concentrated to give a yellow oil. The product was purified by chromatography on silica gel (5% 2M ammonia/methanol in $CH_2Cl_2$) to give the isothiourea (12.5 mg, 23%). The product was dissolved in methanol (1.0 mL) and acidified with 1.0 M HCl in ether (4 mL). The orange precipitate was collected by filtration and washed with hexanes (6.0 mg, 10%). MS (M+1, 435, 437).

Example 43 nNOS, eNOS and iNOS Enzyme Assay

The generation of nitric oxide by NOS was measured using the hemoglobin capture assay (*Proc. Natl. Acad. Sci., U.S.A.* 1990, 87, 714; Huang et al. *J. Med. Chem.* 2000, 43, 2938). An assay mixture for nNOS contained 10 mM L-arginine, 1.6 mM $CaCl_2$, 11.6 mg/mL calmoduline, 100 mM NADPH, 6.5 mM $BH_4$ and 3 mM oxyhemoglobin in 100 mM Hepes (pH 7.5). The reaction mixture for iNOS contained 10 mM of L-arginine, 100 mM NADPH, 6.5 mM $BH_4$ and 3 mM oxyhemoglobin in 100 mM Hepes (pH 7.5). All assays were in a final volume of 600 mL and were initiated with enzyme. Nitric oxide reacts with oxyhemoglobin to yield methehemoglobin which is detected at 401 nm ($\epsilon$=19,700 $M^{-1}cm^{-1}$) on a Perkin-Elmer Lamda 10 UV/vis spectrophotometer.

$IC_{50}$ and percent inhibition of NOS by the compounds of the invention were determined under initial velocity measurement condition with hemoglobin capture assay as described above using varying concentrations of the compounds of the invention. The results are shown in Table 1.

Example 44

Neuroprotection of Rat Cortical Cells Against NMDA Challenge

Rat cortical neuronal cultures were exposed for 30 minutes to 25 μM NMDA in buffer with or without the test compounds according to previously reported procedures (*J. Neurosci.* 2000 October 1; 20(19):7183–92). Test compounds were added for a 60-minute pre-incubation period in order to maximize the chance of seeing neuroprotection. After 24 hrs cultures were treated with propidium iodide and the % cell death determined.

Figure 2:
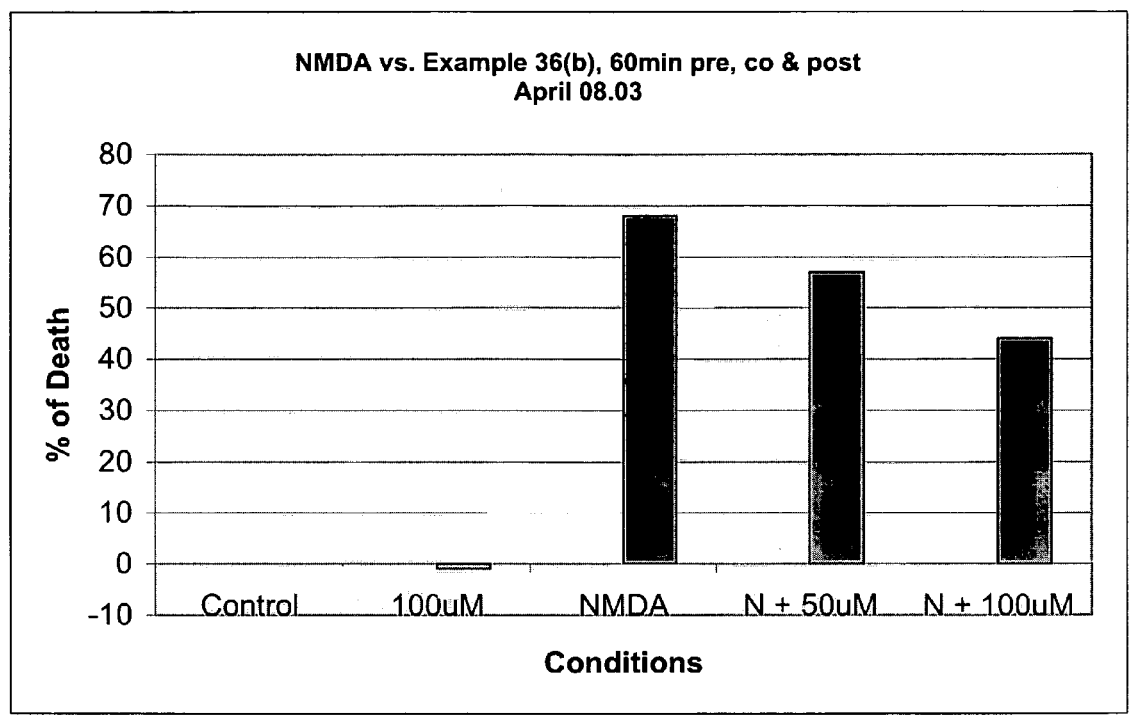
FIG. 2 is a bar graph illustrating the neuroprotection observed during NMDA challenge when rat cortical cells are preincubated with N-[2-(2-morpholin-4-yl-ethylamino)-benzothiazol-6-yl]-thiophene-2-carboxamidine for 60 minutes.

FIG. 1 illustrates the neuroprotection observed during NMDA challenge when rat cortical cells are preincubated with N-{2-[2-(3H-Imidazol-4-yl)-ethylamino]-benzothiazol-6-yl}-thiophene-2-carboxamidine for 60 minutes. FIG. 2 illustrates the neuroprotection observed during NMDA challenge when rat cortical cells are preincubated with N-[2-(2-Morpholin-4-yl-ethylamino)-benzothiazol-6-yl]-thiophene-2-carboxamidine for 60 minutes.

Example 45

Efficacy in Models Predictive of Neuropathic-like Pain States

Figure 3:
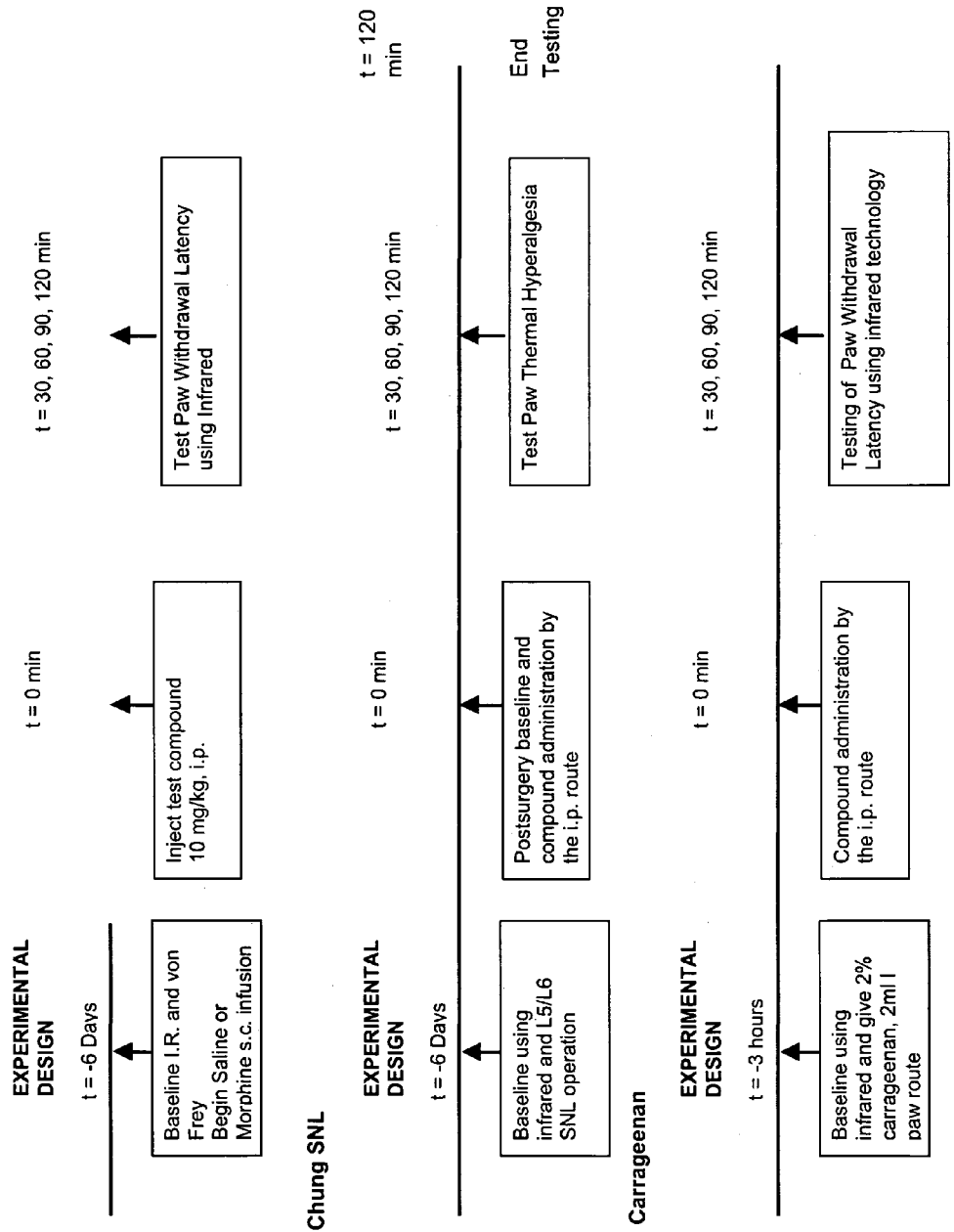
FIG. 3 shows a schematic of the experimental designs for the Morphine-induced Hyperalgesia, Chung Spinal Nerve Ligation (SNL) and Carrageenan Model assays for neuropathic pain.

Confirmation of the usefulness of the compounds of the invention in neuropathic pain states was gathered using standard animal models predictive of antihyperalgesic activity induced by a variety of methods each described in more detail below. The experimental designs for the Morphine-induced Hyperalgesia, Chung Spinal Nerve Ligation SNL and Carrageenan Model assays for neuropathic pain are depicted in FIG. 3.

(a) Chung Model of Injury-Induced Neuropathic-like Pain

Nerve ligation injury was performed according to the method described by Kim and Chung (Kim, S. H. and Chung, J. M. An experimental model for peripheral neuropathy produced by segmental spinal nerve ligation in the rat, Pain 50:355–363, 1992). This technique produces signs of neuropathic dysesthesias, including tactile allodynia, thermal hyperalgesia and guarding of the affected paw. Rats were anesthetized with halothane and the vertebrae over the L4 to S2 region were exposed. The L5 and L6 spinal nerves were exposed, carefully isolated, and tightly ligated with 4-0 silk suture distal to the DRG. After ensuring homeostatic stability, the wounds were sutured, and the animals allowed to recover in individual cages. Sham-operated rats were prepared in an identical fashion except that the L5/L6 spinal nerves were not ligated. Any rats exhibiting signs of motor deficiency will be euthanized.

Figure 4:
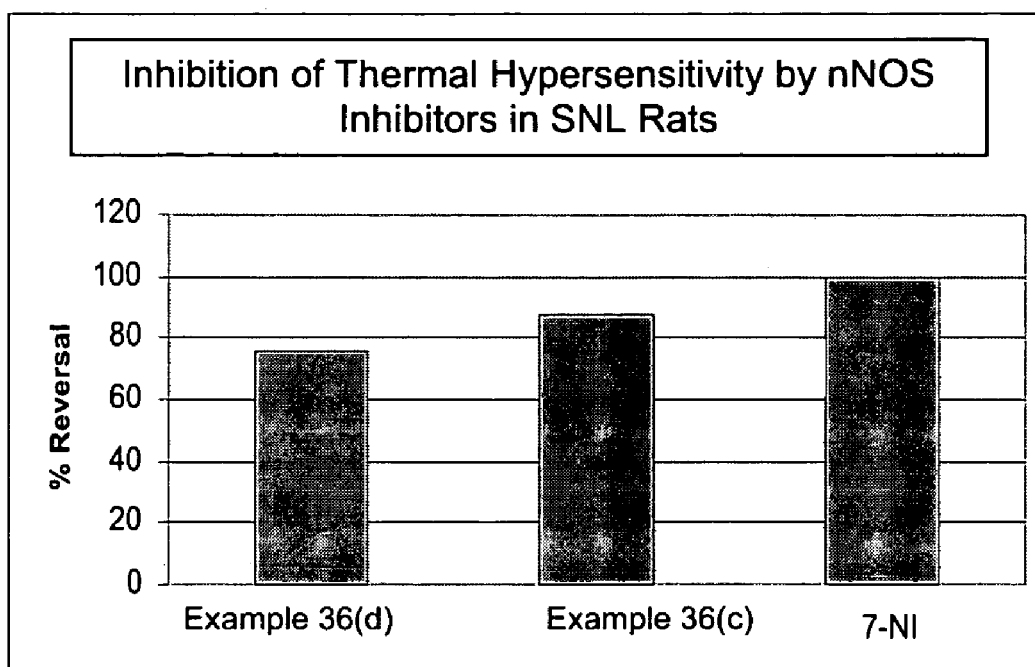
FIG. 4 is a bar graph showing % reversal for the test compounds in the Chung model of pain. % Reversal means the abolition of hyperalgesic response to a thermal stimulus in rats in the Chung model of pain at a standard dose of 10 mg/kg, corrected for molar concentration doses are 18, 22 and 60 micromoles/kg for Example 36(d), Example 36(c) and 7-NI, respectively.

The spinal nerve ligation (SNL) or Chung model is the standard animal model of neuropathic pain following physical injury to nerve fibres (see brief description and reference below). After a period of recovery following the surgical intervention, rats show enhanced sensitivity to painful and normally non-painful stimuli. FIG. 4 shows a summary of experiments involving nNOS inhibitory compounds of the invention in comparison with a non-selective NOS inhibitor. This data reflects the use of one standard dose (10 mg.kg) injected IP according to the procedure listed in the description. There is a clear antihyperalgesic effect of both selective and non-selective compounds, however corrected for molar concentration the example compounds are approximately 3 times more potent than the non-selective NOS inhibitor suggesting an advantage in both dose and efficacy.

(b) Carrageenan-Induced Inflammation as a Model of Primary and Secondary Pain

Inflammation was induced by injecting 0.1 mL of a 2% carrageenan suspension s.c. into the supplanter aspect of a hindpaw of lightly anesthetized rats. Typically, pronounced inflammation and edema were obvious within three hours of the injection.

Figure 5:
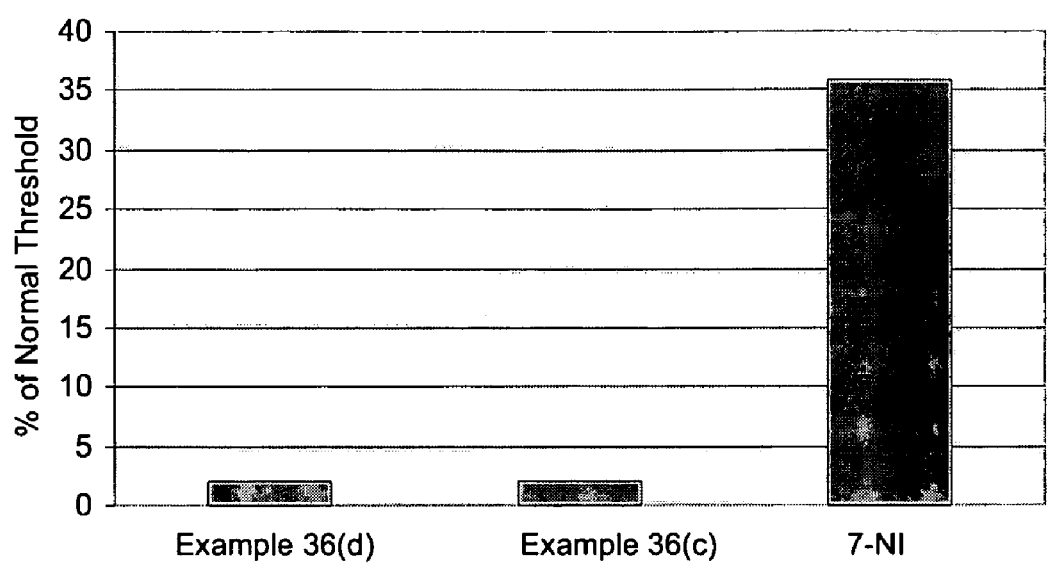
FIG. 5 is a bar graph showing the ativity of example compounds to chemically induced pain. Selective nNOS inhibitors do not change the ability to perceive chemically-induced nocciceptive pain.
Figure 6:
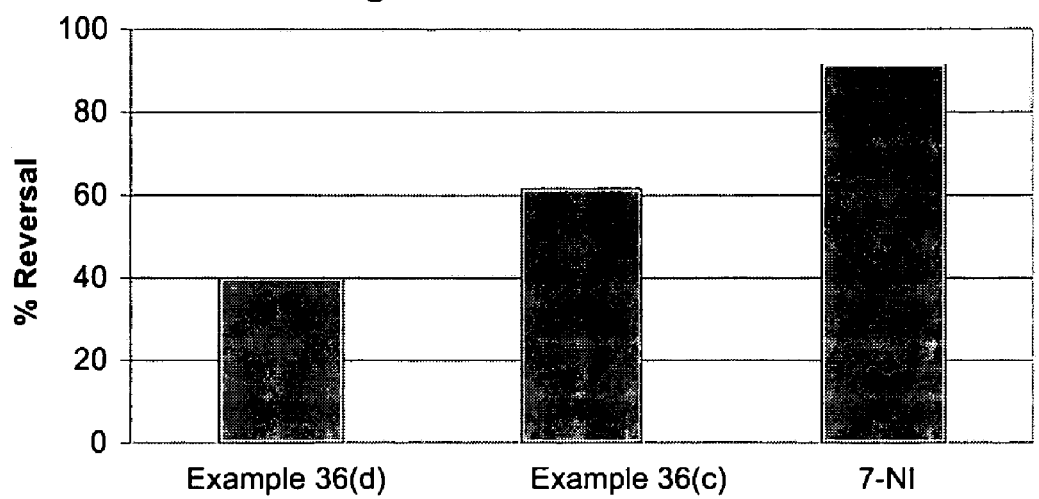
FIG. 6 is a bar graph showing that selective NOS inhibitors reverse the delayed neurogenic hyperalgesia following chemically-induced tissue damage.

The Carrageenan model is a model of inflammatory pain with two components. The first occurring immediately after injection provides information on the acute nociceptive response to a painful stimulus, in this case the chemical carrageenan. There is also a second neurogenic component which develops several hours later and reflects the type of neuronal activity due to the hyperalgesic and allodynic components as found in neuropathic pain. Note, the nNOS selective compounds of the invention are not active during the initial nociceptive phase where the initial inflammatory reponse is dominant (FIG. 5). The non-selective NO inhibitor is active in this component reflecting the lack of selectivity for n vs iNOS. All compounds with nNOS activity are as predicted to be active in the secondary phase and this is clearly illustrated in FIG. 6 at the standard dose.

(c) Morphine-Induced Hyperalgesia

Morphine-induced hyperalgesia was induced by treating rats for 6 days prior to testing with sc infusions of morphine contained in standard Alza osmotic minipumps. Rats were tested on the following day for thermal and tactile hyperalgesia in the usual way. Similar studies have repeatedly demonstrated the reliability of this phenomenon.

Figure 7:
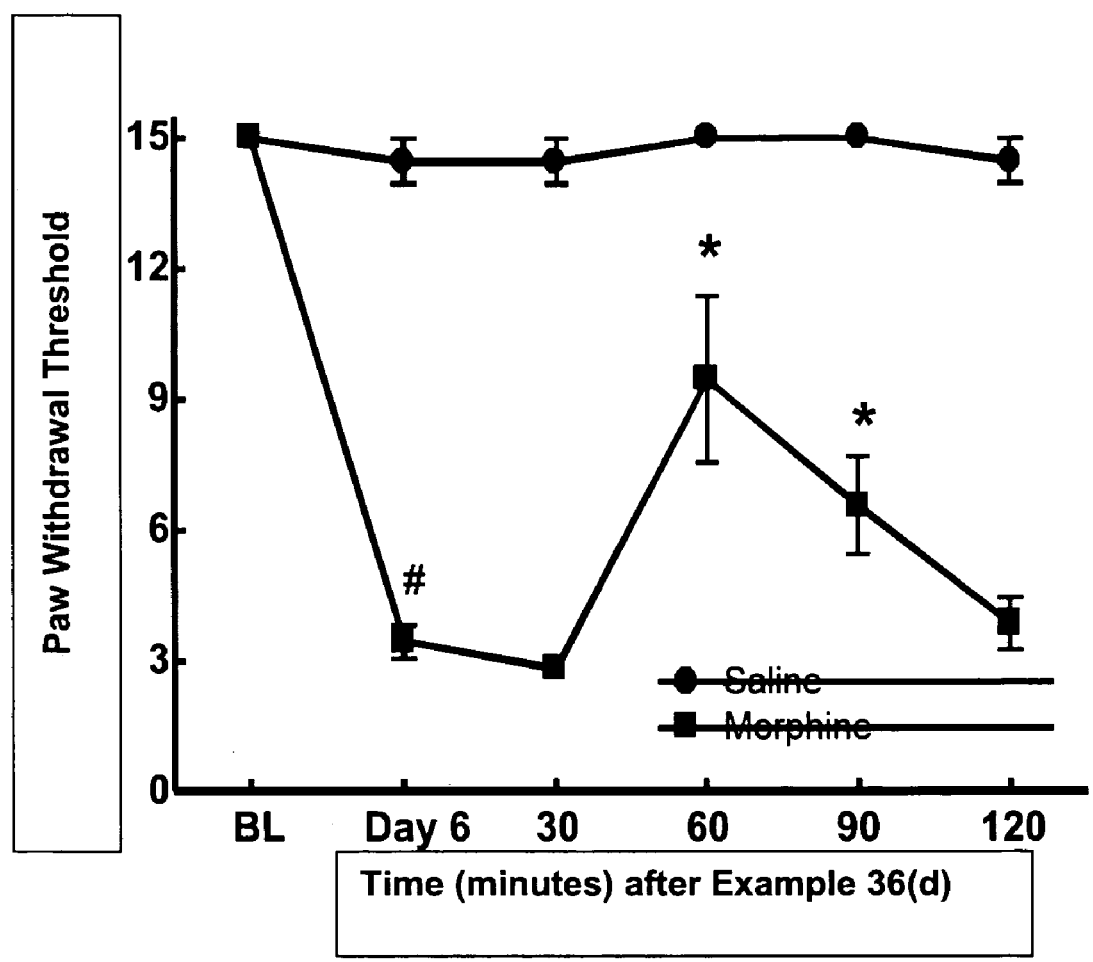
FIG. 7 is a graph showing the ability of example compound at one standard dose (10 mg/kg) to reverse the enhanced sensitivity to tactile stimulus following six days of morphine treatment vs an equivalent saline pretreatment.

The morphine-induced hyperalgesia is a reflection of the changes occurring in the response to pain following chronic opiate treatment and mirrors the development of tolerance to the analgesic effects of opiates such as morphine. In this example, a standard dose of the example compound induces a reversal of the tactile hyperalgesia that has developed under chronic morphine treatment (FIG. 7).

(d) Evaluation of Tactile Allodynia

Mechanical allodynia is determined in the manner described by Chaplan et al. (Chaplan, S. R., Bach, F. W., Pogrel, J. W., Chung J. M. and Yaksh T. L. Quantitative assessment of tactile allodynia in the rat paw. J. Neurosci. Meth. 53:55–63, 1994). The paw withdrawal threshold is determined in response to probing with calibrated von Frey filaments. The rats are kept in suspended cages with wire mesh floors and the von Frey filaments are applied perpendicularly to the plantar surface of the paw of the rat until it buckles slightly, and is held for 3 to 6 sec. A positive response is indicated by a sharp withdrawal of the paw. The 50% paw withdrawal threshold is determined by the non-parametric method of Dixon (Dixon, W. J. Efficient analysis of experimental observations. Ann. Rev. Pharmacol. Toxicol. 20 (1980) 441–462.).

(e) Evaluation of Thermal Hyperalgesia

Thermal hyperalgesia is determined by focusing a radiant heat source onto the plantar surface of the affected paw of nerve-injured or sham-operated rats (Hargreaves. K., Dubner, R., Brown, F., Flores, C. and Joris, J. A new and sensitive method for measuring thermal nociception in cutaneous hyperalgesia. Pain. 32 (1988) 77–88.). When the animal withdraws its paw, a photodetection device halts the stimulus and timer. A maximal cut-off of 40 sec is utilized to prevent tissue damage. Paw withdrawal latencies are thus determined to the nearest 0.1 sec. The withdrawal latency of sham-operated rats will be compared to those of ligated rats to measure the degree of hyperalgesia.

DISCUSSION

Selective nNOS inhibitors, distinguish themselves from non-selective NOS inhibitors by demonstrating usefulness as agents for neuropathic-like pain states whether that has been induced by mechanical or chemical injury, or by the consequences of therapeutic drug treatment. The selective NOS inhibitors also provide these beneficial effects at doses which do not have effects on cardiovascular function due to eNOS inhibition and thus present a major improvement in applicability as a treatment for chronic intractable pain characteristic of neuropathic pain states.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

IC$_{50}$ (μM) of NOS by the Compounds of the invention

| Example Number | nNOS | iNOS | eNOS |
|---|---|---|---|
| 4 | 4.2 | 327 | 83.3 |
| 5 | 1.7 | 26.7 | 17.7 |
| 7 | 250 | — | 238 |
| 9 | 41.4 | — | 119 |
| 13 | 11.9 | 125 | 100 |
| 17 | 32.1 | 275 | 94 |
| 18 | 57.8 | 123 | 145 |
| 20 | 89 | 73 | 169 |
| 36f | 4.8 | >300 | >300 |
| 36b | 1.46 | 91 | 110 |
| 36d | 1.6 | 163 | 210 |

We claim:

1. A compound of Formula I, and pharmaceutically acceptable salts, hydrates, solvates and prodrugs thereof:

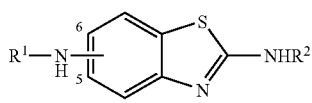

I wherein $R^1$ is selected from the group consisting of:

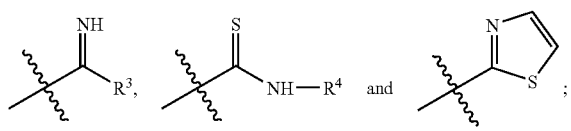

$R^2$ is selected from the group consisting of H,

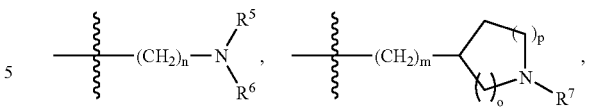

—$(CH_2)_nR^8$ and —$(CH_2)_mR^9$ $R^3$ is selected from the group consisting of $C_{1-6}$alkyl, $SC_{1-6}$alkyl, thienyl and furanyl;

$R^4$ is selected from the group consisting of H, $C_{1-6}$alkyl, Ph, C(O)Ph and —C(O)$C_{1-6}$alkyl;

$R^5$ and $R^6$ are independently selected from the group consisting of H and $C_{1-6}$alkyl or together $R^5$ and $R^6$ and the nitrogen to which they are attached form a 3 to 7-membered azacarbocylic ring wherein one of the carbon atoms in the ring may optionally be replaced with O, S, or $NR^7$;

$R^7$ is selected from the group consisting of H, $C_{1-6}$alkyl, Ph, Heteroaryl, $CH_2$Ph, and $CH_2$Heteroaryl, with Ph and Heteroaryl being optionally substituted with 1–3 groups independently selected from the group consisting of $C_{1-4}$alkyl, halo, OH, $OC_{1-4}$alkyl, $NH_2$, NH($C_{1-4}$alkyl), N($C_{1-4}$alkyl)($C_{1-4}$alkyl), nitro and cyano;

$R^8$ is selected from the group consisting of H, OH, Ph, naphthyl and heteroaryl, with Ph, naphthyl and heteroaryl being optionally substituted with 1–3 groups independently selected from the group consisting of $C_{1-4}$alkyl, halo, $NH_2$, NH($C_{1-4}$alkyl), N($C_{1-4}$alkyl)($C_{1-4}$alkyl), nitro, cyano, OH and $OC_{1-4}$alkyl;

$R^9$ is $C_{3-7}$cycloalkyl optionally substituted with 1–3 groups independently selected from the group consisting of $C_{1-4}$alkyl, halo, $NH_2$, NH($C_{1-4}$alkyl), N($C_{1-4}$alkyl)($C_{1-4}$alkyl), nitro, cyano, OH and $OC_{1-4}$alkyl and one or two of the carbon atoms in $C_{3-7}$cycloalkyl may optionally be replaced with O or S;

n is 1–6;

m is 0–6;

o is 0–2;

p is 1–2; and the group $R^1$NH— is attached to the 5- or 6-position of the aminobenzothiazole ring, with the proviso that, when $R^2$ is H then $R^4$ is not $C_{1-6}$alkyl.

2. The compound according to claim 1, wherein $R^3$ is selected from the group consisting of $C_{1-2}$alkyl, $SC_{1-4}$alkyl and thienyl.

3. The compound according to claim 2, wherein $R^3$ is selected from the group consisting of $SC_{1-2}$alkyl and thienyl.

4. The compound according to claim 1, wherein $R^4$ is selected from the group consisting of H, $C_{1-4}$alkyl, Ph, C(O)Ph and —C(O)$C_{1-4}$alkyl.

5. The compound according to claim 4, wherein $R^4$ is selected from the group consisting of H, and C(O)Ph.

6. The compound according to claim 1, wherein $R^5$ and $R^6$ are independently selected from a group consisting of H and $C_{1-4}$alkyl or together $R^5$ and $R^6$ and the nitrogen to which they are attached form a 4 to 6-membered azacarbocylic ring wherein one of the carbon atoms in the ring may optionally be replaced with O, S, or $NR^7$.

7. The compound according to claim 6, wherein $R^5$ and $R^6$ are independently selected from a group consisting of H and $CH_3$ or together $R^5$ and $R^6$ and the nitrogen to which they are attached form a 5 to 6-membered azacarbocylic ring.

8. The compound according to claim 1, wherein $R^7$ is selected from H, $C_{1-4}$alkyl, Ph, Heteroaryl, $CH_2$Ph, and $CH_2$Heteroaryl, with Ph and Heteroaryl being optionally substituted with 1–2 groups independently selected from the group consisting of $C_{1-4}$alkyl, halo, OH, $OC_{1-4}$alkyl, $NH_2$, $NH(C_{1-4}$alkyl), $N(C_{1-4}$alkyl)($C_{1-4}$alkyl), nitro and cyano.

9. The compound according to claim 8, wherein $R^7$ is selected from H, $C_{1-4}$alkyl, Ph, Heteroaryl, $CH_2$Ph, and $CH_2$Heteroaryl, with Ph and Heteroaryl being optionally substituted with 1 group independently selected from the group consisting of $C_{1-4}$alkyl, halo, OH, $OC_{1-4}$alkyl, $NH_2$, $NH(C_{1-4}$alkyl), $N(C_{1-4}$alkyl)($C_{1-4}$alkyl), nitro and cyano.

10. The compound according to claim 9, wherein $R^7$ is selected from H, Ph, $C_{1-4}$alkyl and $CH_2$Ph, with Ph being optionally substituted with 1 groups independently selected from the group consisting of $C_{1-4}$alkyl, halo, OH, $OC_{1-4}$alkyl, $NH_2$, $NH(C_{1-4}$alkyl), $N(C_{1-4}$alkyl)($C_{1-4}$alkyl), nitro and cyano.

11. The compound according to claim 10, wherein $R^7$ is selected from H, $C_{1-2}$alkyl, Ph and $CH_2$Ph, with Ph being optionally substituted with 1 groups independently selected from the group consisting of methyl, halo, OH, methoxy, $NH_2$, NHMe, $NMe_2$ nitro and cyano.

12. The compound according to claim 11, wherein $R^7$ is selected from methyl and $CH_2$Ph.

13. The compound according to claim 1, wherein $R^8$ is selected from the group consisting of H, OH, Ph and heteroaryl, with Ph and heteroaryl being optionally substituted with 1–2 groups independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl.

14. The compound according to claim 13, wherein $R^8$ is selected from the group consisting of H, OH, Ph, and heteroaryl, with Ph and heteroaryl being optionally substituted with 1 group independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl.

15. The compound according to claim 14, wherein heteroaryl is a 5 or 6 membered aromatic ring.

16. The compound according to claim 15, wherein heteroaryl is selected from pyridyl, imidazolyl, thienyl and furanyl.

17. The compound according to claim 1, wherein $R^9$ is $C_{3-7}$cycloalkyl optionally substituted with 1–2 groups independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl and wherein one of the carbon atoms in $C_{3-7}$cycloalkyl may optionally be replaced with O or S.

18. The compound according to claim 17, wherein $R^9$ is $C_{5-7}$cycloalkyl optionally substituted with 1 group independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl and wherein one of the carbon atoms in $C_{3-7}$cycloalkyl may optionally be replaced with O or S.

19. The compound according to claim 18, wherein $R^9$ is $C_{5-7}$cycloalkyl herein one of the carbon atoms in $C_{3-7}$cycloalkyl may optionally be replaced with O.

20. The compound according to claim 17, wherein $R^9$ is selected from cyclopropyl, cyclobutyl, cyclopentyl, cyclohexyl, cycloheptyl, tetrahydropyranyl and tetrahydrofuran.

21. The compound according to claim 1, wherein n is 1–4.

22. The compound according to claim 21, wherein n is 2.

23. The compound according to claim 1, wherein m is 0–2.

24. The compound according to claim 23, wherein m is 0.

25. The compound according to claim 1, wherein both o and p are 1 to provide a pyrrolidinyl ring.

26. The compound according to claim 1, wherein o is 2 and p is 1, to provide a piperidinyl ring.

27. The compound according to claim 1, wherein $R^1$ is

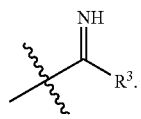

28. The compound according to claim 1, wherein $R^1$ is

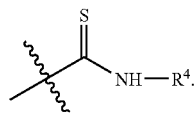

29. The compound according to claim 1 that is selected from the group consisting of:
N-(2-Amino-benzothiazol-6-yl)-methylthiocarboximidamide;
N-(2-Amino-benzothiazol-6-yl)-ethylthiocarboximidamide;
N-(2-Amino-benzothiazol-6-yl)-propylthiocarboximidamide;
N-(2-Amino-benzothiazol-6-yl)-isopropylthiocarboximidamide;
N-(2-Amino-benzothiazol-6-yl)-methylcarboximidamide;
N-(2-Amino-benzothiazol-6-yl)-thiophenecarboximidamide;
N-[2-(2-pyrrolidin-1-ylethylamino)-benzothiazol-6-yl]-2-thiophenecarboximidamide;
1-(2-Amino-benzothiazol-5-yl)-3-benzoyl-thiourea;
1-(2-Amino-benzothiazol-5-yl)-3-ethyl-thiourea;
N-(2-Amino-benzothiazol-5-yl)-thiophene-2-carboxamidine;
N5-Thiazol-2-yl-benzothiazole-2,5-diamine;
(2-Amino-benzothiazol-5-yl)-thiourea;
N-[2-(Tetrahydro-pyran-4-ylamino)-benzothiazol-6-yl]-thiophene-2-carboxamidine;
N-{2-[2-(4-Bromo-phenyl)-ethylamino]-benzothiazol-6-yl}-thiophene-2-carboxamidine;
N-[2-(2-Pyridin-2-yl-ethylamino)-benzothiazol-6-yl]-thiophene-2-carboxamidine;
N-[2-(1-Benzyl-piperidin-4-ylamino)-benzothiazol-6-yl]-thiophene-2-carboxamidine;
N-{2-[2-(3H-Imidazol-4-yl)-ethylamino]-benzothiazol-6-yl}-thiophene-2-carboxamidine;
N-[2-(2-Morpholin-4-yl-ethylamino)-benzothiazol-6-yl]-thiophene-2-carboxamidine;
N-[2-(2-Dimethylamino-ethylamino)-benzothiazol-5-yl]-thiophene-2-carboxamidine;
N-{2-[2-(1-Methyl-pyrrolidin-2-yl)-ethylamino]-benzothiazol-5-yl}-thiophene-2-carboxamidine;
N-{2-[2-(3-Chloro-phenyl)-ethylamino]-benzothiazol-6-yl}-thiophene-2-carboxamidine;
N-[2-(4-Hydroxy-butylamino)-benzothiazol-6-yl]-thiophene-2-carboxamidine;
N-[2-(3-Imidazol-1-yl-propylamino)-benzothiazol-6-yl]-thiophene-2-carboxamidine;
N2-(1-Benzyl-piperidin-4-yl)-N-6-thiazol-2-yl-benzothiazole-2,6-diamine;
1-Benzoyl-3-{2-[2-(4-bromo-phenyl)-ethylamino]-benzothiazol-6-yl}-thiourea;

{2-[2-(4-Bromo-phenyl)-ethylamino]-benzothiazol-6-yl}-thiourea; and

1-{2-[2-(4-Bromo-phenyl)-ethylamino]-benzothiazol-6-yl}-2-ethyl-isothiourea.

30. A pharmaceutical composition comprising a compound according to claim 1 and a pharmaceutically acceptable carrier.

31. A pharmaceutical composition comprising a compound according to claim 29 and a pharmaceutically acceptable carrier.

32. A method of treating, or reducing the risk of, a disease or condition which benefits from an inhibition of NOS activity comprising administering an effective amount of a compound of Formula I according to claim 1 to a cell or animal in need thereof, wherein the disease or condition is selected from the group consisting of migraine, a reversible obstructive airway disease, asthma, adult respiratory distress syndrome (ARDS), stroke, neurological deficits associated with coronary artery bypass graft (CABG), chronic pain, neuropathic pain, traumatic shock, reperfusion injury, multiple sclerosis, AIDS associated dementia, neuron toxicity, alcohol dependency, nicotine dependency, opioid induced tolerance and withdrawal symptoms, epilepsy, anxiety, head trauma, acute spinal cord injury, Huntington's disease, Parkinson's disease, Alzheimer's disease, glaucoma, macular degeneration, neurodegeneration and diabetic nephropathy.

33. The method according to claim 32, wherein the disease or condition that benefits from an inhibition of NOS activity is selected from the group consisting of stroke, reperfusion injury, neurodegeneration, head trauma, neurological deficits associated with CABG, migraine, neuropathic pain and chronic pain.

34. The method according to claim 33, wherein the disease or condition that benefits from an inhibition of NOS activity is neuropathic pain.

35. The method according to claim 33, wherein the disease or condition that benefits from an inhibition of NOS activity is migraine.

36. The method according to claim 33, wherein the disease or condition that benefits from an inhibition of NOS activity is stroke.

37. The method according to claim 33, wherein the disease or condition that benefits from an inhibition of NOS activity is opioid induced tolerance and withdrawal symptoms.

38. The method according to claim 32, wherein $R^3$ in the compound of Formula I is selected from the group consisting of $C_{1-2}$alkyl, $SC_{1-4}$alkyl and thienyl.

39. The method according to claim 38, wherein $R^3$ is selected from the group consisting of $SC_{1-2}$alkyl and thienyl.

40. The method according to claim 32, wherein $R^4$ in the compound of Formula I is selected from the group consisting of H, $C_{1-4}$alkyl, Ph, C(O)Ph and —C(O)$C_{1-4}$alkyl.

41. The method according to claim 38, wherein $R^4$ in the compound of Formula I is selected from the group consisting of H, and C(O)Ph.

42. The method according to claim 32, wherein $R^5$ and $R^6$ in the compound of Formula I are independently selected from a group consisting of H and $C_{1-4}$alkyl or together $R^5$ and $R^6$ and the nitrogen to which they are attached form a 4 to 6-membered azacarbocylic ring wherein one of the carbon atoms in the ring may optionally be replaced with O, S, or $NR^7$.

43. The method according to claim 42, wherein $R^5$ and $R^6$ in the compound of Formula I are independently selected from a group consisting of H and $CH_3$ or together $R^5$ and $R^6$ and the nitrogen to which they are attached form a 5 to 6-membered azacarbocylic ring.

44. The method according to claim 32, wherein in the compound of Formula I $R^7$ is selected from H, $C_{1-4}$alkyl, Ph, Heteroaryl, $CH_2$Ph, and $CH_2$Heteroaryl, with Ph and Heteroaryl being optionally substituted with 1–2 groups independently selected from the group consisting of $C_{1-4}$alkyl, halo, OH, $OC_{1-4}$alkyl, $NH_2$, $NH(C_{1-4}$alkyl), $N(C_{1-4}$alkyl)($C_{1-4}$alkyl), nitro and cyano.

45. The method according to claim 44, wherein in the compound of Formula I $R^7$ is selected from H, $C_{1-4}$alkyl, Ph, Heteroaryl, $CH_2$Ph, and $CH_2$Heteroaryl, with Ph and Heteroaryl being optionally substituted with 1 group independently selected from the group consisting of $C_{1-4}$alkyl, halo, OH, $OC_{1-4}$alkyl, $NH_2$, $NH(C_{1-4}$alkyl), $N(C_{1-4}$alkyl)($C_{1-4}$alkyl), nitro and cyano.

46. The method according to claim 45, wherein in the compound of Formula I $R^7$ is selected from H, Ph, $C_{1-4}$alkyl and $CH_2$Ph, with Ph being optionally substituted with 1 groups independently selected from the group consisting of $C_{1-4}$alkyl, halo, OH, $OC_{1-4}$alkyl, $NH_2$, $NH(C_{1-4}$alkyl), $N(C_{1-4}$alkyl)($C_{1-4}$alkyl), nitro and cyano.

47. The method according to claim 46, wherein in the compound of Formula I $R^7$ is selected from H, $C_{1-2}$alkyl, Ph and $CH_2$Ph, with Ph being optionally substituted with 1 groups independently selected from the group consisting of methyl, halo, OH, methoxy, $NH_2$, NHMe, $NMe_2$ nitro and cyano.

48. The method according to claim 47, wherein in the compound of Formula I $R^7$ is selected from methyl and $CH_2$Ph.

49. The method according to claim 32, wherein in the compound of Formula I $R^8$ is selected from the group consisting of H, OH, Ph and heteroaryl, with Ph and heteroaryl being optionally substituted with 1–2 groups independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl.

50. The method according to claim 49, wherein in the compound of Formula I $R^8$ is selected from the group consisting of H, OH, Ph, and heteroaryl, with Ph and heteroaryl being optionally substituted with 1 group independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl.

51. The method according to claim 50, wherein in the compound of Formula I heteroaryl is a 5 or 6 membered aromatic ring.

52. The method according to claim 51, wherein in the compound of Formula I heteroaryl is selected from pyridyl, imidazolyl, thienyl and furanyl.

53. The method according to claim 32, wherein in the compound of Formula I $R^9$ is $C_{3-7}$cycloalkyl optionally substituted with 1–2 groups independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl and wherein one of the carbon atoms in $C_{3-7}$cycloalkyl may optionally be replaced with O or S.

54. The method according to claim 53, wherein in the compound of Formula I $R^9$ is $C_{5-7}$cycloalkyl optionally substituted with 1 group independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl and wherein one of the carbon atoms in $C_{3-7}$cycloalkyl may optionally be replaced with O or S.

55. The method according to claim 54, wherein in the compound of Formula I $R^9$ is $C_{5-7}$cycloalkyl herein one of the carbon atoms in $C_{3-7}$cycloalkyl may optionally be replaced with O.

56. The method according to claim 55, wherein in the compound of Formula I $R^9$ is selected from cyclopropyl, cyclobutyl, cyclopentyl, cyclohexyl, cycloheptyl, tetrahydropyranyl and tetrahydrofuran.

57. The method according to claim 32, wherein in the compound of Formula I n is 1–4.

58. The method according to claim 57, wherein in the compound of Formula I n is 2.

59. The method according to claim 32, wherein in the compound of Formula I m is 0–2.

60. The method according to claim 59, wherein in the compound of Formula I m is 0.

61. The method according to claim 32, wherein in the compound of Formula I both o and p are 1 to provide a pyrrolidinyl ring.

62. The method according to claim 32, wherein in the compound of Formula I o is 2 and p is 1 to provide a piperidinyl ring.

63. The method according to claim 32, wherein in the compound of Formula I $R^1$ is

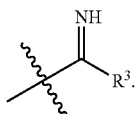

64. The method according to claim 32, wherein in the compound of Formula I $R^1$ is

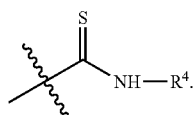

65. The method according to claim 63, wherein $R^3$ is selected from the group consisting of thienyl and furanyl.

66. The method according to claim 65, wherein in the compound of Formula I, $R^2$ is

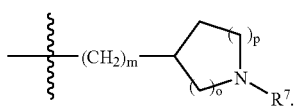

67. The method according to claim 66, wherein m is 0.

68. The method according to claim 67, wherein o is 2 and p is 1 to provide a piperidinyl ring.

69. The method according to claim 68, wherein $R^7$ is $CH_2Ph$ and Ph is optionally substituted with 1–3 groups independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl.

70. The method according to claim 69, wherein $R^7$ is $CH_2Ph$ and Ph is optionally substituted with 1 group selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl.

71. The method according to claim 70, wherein $R^7$ is $CH_2Ph$ and Ph is substituted with halo.

72. The method according to claim 32, wherein, in the compound of Formula I, heteroaryl is selected from the group consisting of pyridinyl, imidazolyl, thienyl, furanyl, indolyl, isoquinolinyl, quinolinyl, benzothienyl and benzofuranyl.

73. The method according to claim 32, wherein, in the compound of Formula I, $C_{3-7}$cycloalkyl is selected from the group consisting of cyclopropyl, cyclobutyl, cyclopentyl, cyclohexyl and cycloheptyl, wherein, in each of the latter groups, one or two of the carbon atoms is optionally replaced with O or S.

74. The method according to claim 32, wherein in the compound of Formula I, the 3- to 7-membered azacarbocyclic ring is selected from the group consisting of pyrolidine, piperazine and homopiperazine wherein, in each of the latter groups, one of the carbon atoms is optionally replaced with O, S or $NR^7$.

75. The method according to claim 32 wherein the compound of Formula I is selected from the group consisting of:
N-(2-Amino-benzothiazol-6-yl)-methylthiocarboximidamide;
N-(2-Amino-benzothiazol-6-yl)-ethylthiocarboximidamide;
N-(2-Amino-benzothiazol-6-yl)-propylthiocarboximidamide;
N-(2-Amino-benzothiazol-6-yl)-isopropylthiocarboximidamide;
N-(2-Amino-benzothiazol-6-yl)-methylcarboximidamide;
N-(2-Amino-benzothiazol-6-yl)-2-thiophenecarboximidamide;
N-[2-(2-pyrrolidin-1-ylethylamino)-benzothiazol6yl]-2-thiophenecarboximidamide;
1-(2-Amino-benzothiazol-5-yl)-3-benzoyl-thiourea;
1-(2-Amino-benzothiazol-5-yl)-3-ethyl-thiourea;
N-(2-Amino-benzothiazol-5-yl)-thiophene-2carboxamidine;
N5-Thiazol-2-yl-benzothiazole-2,5-diamine;
(2-Amino-benzothiazol-5-yl)-thiourea;
N-[2-(Tetrahydro-pyran-4-ylamino)-benzothiazol-6-yl]-thiophene-2carboxamidine;
N-{2-[2-(4-Bromo-phenyl)-ethylamino]-benzothiazol-6-yl}-thiophene-2-carboxamidine;
N-[2-(2-Pyridin-2-yl-ethylamino)-benzothiazol-6-yl]-thiophene-2-carboxamidine;
N-[2-(1-Benzyl-piperidin-4-ylamino)-benzothiazol-6-yl]-thiophene-2-carboxamidine;
N-{2-[2-(3H-Imidazol-4-yl)-ethylamino]-benzothiazol-6-yl}-thiophene-2-carboxamidine;
N-[2-(2-Morpholin-4-yl-ethylamino)-benzothiazol-6-yl]-thiophene-2-carboxamidine;
N-[2-(2-Dimethylamino-ethylamino)-benzothiazol-5-yl]-thiophene-2-carboxamidine;
N-{2-[2-(1-Methyl-pyrrolidin-2-yl)-ethylamino]-benzothiazol-5-yl}-thiophene-2-carboxamidine;
N-{2-[2-(3-Chloro-phenyl)-ethylamino]-benzothiazol-6-yl}-thiophene-2-carboxamidine;
N-[2-(4-Hydroxy-butylamino)-benzothiazol-6-yl]-thiophene-2-carboxamidine;

N-[2-(3-Imidazol-1-yl-propylamino)-benzothiazol-6-yl]-thiophene-2-carboxamidine;

N2-(1-Benzyl-piperidin-4-yl)-N6-thiazol-2-yl-benzothiazole-2,6-diamine;

1-Benzoyl-3-{2-[2-(4-bromo-phenyl)-ethylamino]-benzothiazol-6-yl}-thiourea;

{2-[2-(4-Bromo-phenyl)-ethylamino]-benzothiazol-6-yl}-thiourea; and

1-{2-[2-(4-Bromo-phenyl)-ethylamino]-benzothiazol-6yl}-2ethyl-isothiourea.

76. The compound according to claim 27, wherein $R^3$ is selected from the group consisting of thienyl and furanyl.

77. The compound according to claim 76, wherein $R^2$ is

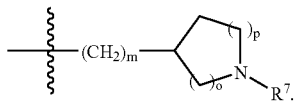

78. The compound according to claim 77, wherein m is 0.

79. The compound according to claim 78, wherein o is 2 and p is 1 to provide a piperidinyl ring.

80. The compound according to claim 79, wherein $R^7$ is $CH_2Ph$ and Ph is optionally substituted with 1–3 groups independently selected from the group consisting of $C_{1-4}$alkyl, halo, $NH_2$, $NH(C_{1-4}$alkyl), $N(C_{1-4}$alkyl)($C_{1-4}$alkyl), nitro, cyano, OH and $OC_{1-4}$alkyl.

81. The compound according to claim 80, wherein $R^7$ is $CH_2Ph$ and Ph is optionally substituted with 1 group selected from the group consisting of $C_{1-4}$alkyl, halo, $NH_2$, $NH(C_{1-4}$alkyl), $N(C_{1-4}$alkyl)($C_{1-4}$alkyl) nitro, cyano, OH and $OC_{1-4}$alkyl.

82. The compound according to claim 81, wherein $R^7$ is $CH_2Ph$ and Ph is substituted with halo.

83. The compound according to claim 1, wherein heteroaryl is selected from the group consisting of pyridinyl, imidazolyl, thienyl, furanyl, indolyl, isoquinolinyl, quinolinyl, benzothienyl and benzofuranyl.

84. The compound according to claim 1, wherein $C_{3-7}$cycloalkyl is selected from the group consisting of cyclopropyl, cyclobutyl, cyclopentyl, cyclohexyl and cycloheptyl, wherein, in each of the latter groups, one or two of the carbon atoms is optionally replaced with O or S.

85. The compound according to claim 1, wherein the 3- to 7-membered azacarbocyclic ring is selected from the group consisting of pyrolidine, piperazine and homopiperazine, wherein, in each of the latter groups, one of the carbon atoms is optionally replaced with O, S or $NR^7$.

* * * * *